(12) United States Patent
Myers et al.

(10) Patent No.: US 11,135,216 B2
(45) Date of Patent: *Oct. 5, 2021

(54) SUBLINGUAL AND BUCCAL FILM COMPOSITIONS

(71) Applicant: INDIVIOR UK LIMITED, Hull (GB)

(72) Inventors: Garry L. Myers, Kingsport, TN (US); Samuel D. Hilbert, Jonesboro, TN (US); Bill J. Boone, Johnson City, TN (US); Beuford Arlie Bogue, Valparaiso, IN (US); Pradeep Sanghvi, Valparaiso, IN (US); Madhusudan Hariharan, Munster, IN (US)

(73) Assignee: Indivior UK Limited, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/439,530

(22) Filed: Jun. 12, 2019

(65) Prior Publication Data

US 2020/0030313 A1    Jan. 30, 2020

Related U.S. Application Data

(63) Continuation of application No. 15/483,769, filed on Apr. 10, 2017, now abandoned, which is a continuation of application No. 14/989,669, filed on Jan. 6, 2016, now Pat. No. 9,687,454, which is a continuation of application No. 14/715,462, filed on May 18, 2015, now abandoned, which is a continuation of application No. 14/478,786, filed on Sep. 5, 2014, now abandoned, which is a continuation of application No. 13/964,975, filed on Aug. 12, 2013, now abandoned, which is a continuation of application No. 13/923,749, filed on Jun. 21, 2013, now abandoned, which is a continuation of application No. 12/537,571, filed on Aug. 7, 2009, now Pat. No. 8,475,832.

(51) Int. Cl.

| | |
|---|---|
| *A61K 31/485* | (2006.01) |
| *A61K 9/00* | (2006.01) |
| *A61K 31/4355* | (2006.01) |
| *A61K 9/70* | (2006.01) |
| *A61K 47/34* | (2017.01) |
| *A61K 31/46* | (2006.01) |
| *A61K 47/32* | (2006.01) |
| *A61K 47/10* | (2017.01) |
| *A61K 47/12* | (2006.01) |
| *A61K 47/22* | (2006.01) |
| *A61K 47/26* | (2006.01) |
| *A61K 47/38* | (2006.01) |

(52) U.S. Cl.
CPC ............ *A61K 31/485* (2013.01); *A61K 9/006* (2013.01); *A61K 9/0056* (2013.01); *A61K 9/7007* (2013.01); *A61K 31/4355* (2013.01); *A61K 31/46* (2013.01); *A61K 47/10* (2013.01); *A61K 47/12* (2013.01); *A61K 47/22* (2013.01); *A61K 47/26* (2013.01); *A61K 47/32* (2013.01); *A61K 47/34* (2013.01); *A61K 47/38* (2013.01)

(58) Field of Classification Search
CPC ............ A61K 2300/00; A61K 31/4355; A61K 31/485; A61K 31/46; A61K 47/32; A61K 47/34; A61K 9/0056; A61K 9/006; A61K 9/7007
USPC ...... 514/282, 279, 289, 646, 317, 329, 18.3; 424/400, 465, 472, 490, 484; 525/54.1, 525/54.2, 185, 415, 420

See application file for complete search history.

(56) References Cited

U.S. PATENT DOCUMENTS

| | | |
|---|---|---|
| 307,537 A | 11/1884 | Foulks |
| 688,446 A | 12/1901 | Stempel |
| 2,980,554 A | 4/1961 | Gentile et al. |
| 3,007,848 A | 11/1961 | Stoop |
| 3,249,109 A | 5/1966 | Maeth et al. |
| 3,444,858 A | 5/1969 | Russell |
| 3,536,809 A | 10/1970 | Applezweig |
| 3,551,556 A | 12/1970 | Kliment et al. |
| 3,598,122 A | 8/1971 | Zaffaroni |
| 3,632,740 A | 1/1972 | Robinson et al. |
| 3,640,741 A | 2/1972 | Etes |
| 3,641,237 A | 2/1972 | Gould et al. |
| 3,731,683 A | 5/1973 | Zaffaroni |
| 3,753,732 A | 8/1973 | Boroshok |
| 3,814,095 A | 6/1974 | Lubens |
| 3,892,905 A | 7/1975 | Albert |

(Continued)

FOREIGN PATENT DOCUMENTS

| | | |
|---|---|---|
| AU | 741362 B2 | 7/1998 |
| DE | 2432925 B2 | 1/1976 |

(Continued)

OTHER PUBLICATIONS

Al-Ghananeem, A. et al. (2006). "Effect of pH on Sublingual Absorption of Oxycodone Hydrochloride." AAPS PharmSciTech 7(1) Article 23 (http://www.aapspharmscitech.org).

(Continued)

*Primary Examiner* — Janet L Epps-Smith
(74) *Attorney, Agent, or Firm* — Lisa E. Stahl; Kathryn Jones

(57) ABSTRACT

The present invention relates to products and methods for treatment of narcotic dependence in a user. The invention more particularly relates to self-supporting dosage forms which provide an active agent for treating narcotic dependence while providing sufficient buccal adhesion of the dosage form.

9 Claims, No Drawings

(56) References Cited

U.S. PATENT DOCUMENTS

| | | |
|---|---|---|
| 3,911,099 A | 10/1975 | DeFoney et al. |
| 3,972,995 A | 8/1976 | Tsuk et al. |
| 3,980,766 A | 9/1976 | Shaw et al. |
| 3,996,934 A | 12/1976 | Zaffaroni |
| 4,029,757 A | 6/1977 | Mlodozeniec et al. |
| 4,029,758 A | 6/1977 | Mlodozeniec et al. |
| 4,031,200 A | 6/1977 | Reif |
| 4,070,494 A | 1/1978 | Hoffmeister et al. |
| 4,123,592 A | 10/1978 | Rainer et al. |
| 4,128,445 A | 12/1978 | Sturzenegger et al. |
| 4,136,145 A | 1/1979 | Fuchs et al. |
| 4,136,162 A | 1/1979 | Fuchs et al. |
| 4,139,627 A | 2/1979 | Lane et al. |
| 4,226,848 A | 10/1980 | Nagai et al. |
| 4,251,400 A | 2/1981 | Columbus |
| 4,259,686 A | 3/1981 | Suzuki et al. |
| 4,292,299 A | 9/1981 | Suzuki et al. |
| 4,294,820 A | 10/1981 | Keith et al. |
| 4,302,465 A | 11/1981 | AF Ekenstam et al. |
| 4,307,075 A | 12/1981 | Martin |
| 4,325,855 A | 4/1982 | Dickmann et al. |
| 4,373,036 A | 2/1983 | Chang et al. |
| 4,406,708 A | 9/1983 | Hesselgren |
| 4,432,975 A | 2/1984 | Libby |
| 4,438,258 A | 3/1984 | Graham |
| 4,460,562 A | 7/1984 | Keith et al. |
| 4,466,973 A | 8/1984 | Rennie |
| 4,503,070 A | 3/1985 | Eby, III |
| 4,515,162 A | 5/1985 | Yamamoto et al. |
| 4,517,173 A | 5/1985 | Kizawa et al. |
| 4,529,601 A | 7/1985 | Broberg et al. |
| 4,529,748 A | 7/1985 | Wienecke |
| 4,562,020 A | 12/1985 | Hijiya et al. |
| 4,569,837 A | 2/1986 | Suzuki et al. |
| 4,582,835 A | 4/1986 | Lewis et al. |
| 4,593,053 A | 6/1986 | Jevne et al. |
| 4,608,249 A | 8/1986 | Otsuka et al. |
| 4,615,697 A | 10/1986 | Robinson |
| 4,623,394 A | 11/1986 | Nakamura et al. |
| 4,631,837 A | 12/1986 | Magoon |
| 4,652,060 A | 3/1987 | Miyake |
| 4,659,714 A | 4/1987 | Watt-Smith |
| 4,661,492 A | 4/1987 | Lewis et al. |
| 4,675,009 A | 6/1987 | Hymes et al. |
| 4,695,465 A | 9/1987 | Kigasawa et al. |
| 4,704,119 A | 11/1987 | Shaw et al. |
| 4,713,239 A | 12/1987 | Babaian et al. |
| 4,713,243 A | 12/1987 | Schiraldi et al. |
| 4,722,761 A | 2/1988 | Cartmell et al. |
| 4,740,365 A | 4/1988 | Yukimatsu et al. |
| 4,748,022 A | 5/1988 | Busciglio |
| 4,755,386 A | 7/1988 | Hsiao et al. |
| 4,765,983 A | 8/1988 | Takayanagi et al. |
| 4,772,470 A | 9/1988 | Inoue et al. |
| 4,777,046 A | 10/1988 | Iwakura et al. |
| 4,789,667 A | 12/1988 | Makino et al. |
| 4,849,246 A | 7/1989 | Schmidt |
| 4,860,754 A | 8/1989 | Sharik et al. |
| RE33,093 E | 10/1989 | Schiraldi et al. |
| 4,876,092 A | 10/1989 | Mizobuchi et al. |
| 4,876,970 A | 10/1989 | Bolduc |
| 4,888,354 A | 12/1989 | Chang et al. |
| 4,894,232 A | 1/1990 | Reul et al. |
| 4,900,552 A | 2/1990 | Sanvordeker et al. |
| 4,900,554 A | 2/1990 | Yanagibashi et al. |
| 4,900,556 A | 2/1990 | Wheatley et al. |
| 4,910,247 A | 3/1990 | Haldar et al. |
| 4,915,950 A | 4/1990 | Miranda et al. |
| 4,925,670 A | 5/1990 | Schmidt |
| 4,927,634 A | 5/1990 | Sorrentino et al. |
| 4,927,636 A | 5/1990 | Hijiya et al. |
| 4,935,428 A | 6/1990 | Lewis |
| 4,937,078 A | 6/1990 | Mezei et al. |
| 4,940,587 A | 7/1990 | Jenkins et al. |
| 4,948,580 A | 8/1990 | Browning |
| 4,958,580 A | 9/1990 | Asaba et al. |
| 4,978,531 A | 12/1990 | Yamazaki et al. |
| 4,981,693 A | 1/1991 | Higashi et al. |
| 4,981,875 A | 1/1991 | Leusner et al. |
| 4,992,277 A | 2/1991 | Sangekar et al. |
| 5,023,082 A | 6/1991 | Friedman et al. |
| 5,024,701 A | 6/1991 | Desmarais |
| 5,028,632 A | 7/1991 | Fuisz |
| 5,045,445 A | 9/1991 | Schultz |
| 5,047,244 A | 9/1991 | Sanvordeker et al. |
| 5,064,717 A | 11/1991 | Suzuki et al. |
| 5,089,307 A | 2/1992 | Ninomiya et al. |
| 5,118,508 A | 6/1992 | Kikuchi et al. |
| 5,139,790 A | 8/1992 | Snipes |
| 5,158,825 A | 10/1992 | Altwirth |
| 5,166,233 A | 11/1992 | Kuroya et al. |
| 5,186,938 A | 2/1993 | Sablotsky et al. |
| 5,229,164 A | 7/1993 | Pins et al. |
| 5,234,957 A | 8/1993 | Mantelle |
| 5,271,940 A | 12/1993 | Cleary et al. |
| 5,272,191 A | 12/1993 | Ibrahim et al. |
| 5,273,758 A | 12/1993 | Royce |
| 5,288,497 A * | 2/1994 | Stanley ................ A23G 3/368 424/440 |
| 5,346,701 A | 9/1994 | Heiber et al. |
| 5,354,863 A | 10/1994 | Dappen et al. |
| 5,393,528 A | 2/1995 | Staab |
| 5,411,945 A | 5/1995 | Ozaki et al. |
| 5,413,792 A | 5/1995 | Ninomiya et al. |
| 5,433,960 A | 7/1995 | Meyers |
| 5,455,043 A | 10/1995 | Fischel-Ghodsian |
| 5,462,749 A | 10/1995 | Rencher |
| 5,472,704 A | 12/1995 | Santus et al. |
| 5,518,902 A | 5/1996 | Ozaki et al. |
| 5,567,431 A | 10/1996 | Vert et al. |
| 5,605,696 A | 2/1997 | Eury et al. |
| 5,620,757 A | 4/1997 | Ninomiya et al. |
| 5,629,003 A | 5/1997 | Horstmann et al. |
| 5,681,873 A | 10/1997 | Norton et al. |
| 5,700,478 A | 12/1997 | Biegajski et al. |
| 5,700,479 A | 12/1997 | Lundgren |
| 5,702,725 A | 12/1997 | Merrill et al. |
| 5,766,332 A | 6/1998 | Graves et al. |
| 5,766,620 A | 6/1998 | Heiber et al. |
| 5,766,623 A | 6/1998 | Ayres et al. |
| 5,766,839 A | 6/1998 | Johnson et al. |
| 5,800,832 A | 9/1998 | Tapolsky et al. |
| 5,806,284 A | 9/1998 | Gifford |
| 5,891,461 A | 4/1999 | Jona et al. |
| 5,900,247 A | 5/1999 | Rault et al. |
| 5,948,430 A | 9/1999 | Zerbe et al. |
| 6,072,100 A | 6/2000 | Mooney et al. |
| 6,103,266 A | 8/2000 | Tapolsky et al. |
| 6,124,282 A | 9/2000 | Sellers et al. |
| 6,126,969 A | 10/2000 | Shah et al. |
| 6,153,210 A | 11/2000 | Roberts et al. |
| 6,159,498 A | 12/2000 | Tapolsky et al. |
| 6,177,096 B1 | 1/2001 | Zerbe et al. |
| 6,228,863 B1 | 5/2001 | Palermo et al. |
| 6,231,957 B1 | 5/2001 | Zerbe et al. |
| 6,264,981 B1 | 7/2001 | Zhang et al. |
| 6,284,264 B1 | 9/2001 | Zerbe et al. |
| 6,344,212 B2 | 2/2002 | Reder et al. |
| 6,375,963 B1 | 4/2002 | Repka et al. |
| 6,503,532 B1 | 1/2003 | Murty et al. |
| 6,667,060 B1 | 12/2003 | Vandecruys et al. |
| 6,800,329 B2 | 10/2004 | Horstmann et al. |
| 6,824,829 B2 | 11/2004 | Berry et al. |
| 6,995,169 B2 | 2/2006 | Chapleo et al. |
| 7,005,142 B2 | 2/2006 | Leon et al. |
| 7,357,891 B2 | 4/2008 | Yang et al. |
| 7,425,292 B2 | 9/2008 | Yang et al. |
| 7,579,019 B2 | 8/2009 | Tapolsky et al. |
| 8,147,866 B2 * | 4/2012 | Finn ................ A61K 9/0056 424/435 |
| 8,475,832 B2 * | 7/2013 | Myers ................ A61P 25/36 424/435 |
| 9,101,625 B2 | 8/2015 | Oksche et al. |
| 9,370,512 B2 | 6/2016 | Oksche et al. |

(56) References Cited

U.S. PATENT DOCUMENTS

| | | |
|---|---|---|
| 2001/0006677 A1 | 7/2001 | McGinity et al. |
| 2001/0022964 A1 | 9/2001 | Leung et al. |
| 2001/0046511 A1 | 11/2001 | Zerbe et al. |
| 2002/0187192 A1 | 12/2002 | Joshi et al. |
| 2003/0069263 A1 | 4/2003 | Breder et al. |
| 2003/0107149 A1 | 6/2003 | Yang et al. |
| 2003/0124176 A1 | 7/2003 | Hsu et al. |
| 2004/0096569 A1 | 5/2004 | Barkalow et al. |
| 2004/0191302 A1 | 9/2004 | Davidson |
| 2005/0037055 A1 | 2/2005 | Yang et al. |
| 2005/0042281 A1 | 2/2005 | Singh et al. |
| 2005/0048102 A1 | 3/2005 | Tapolsky et al. |
| 2005/0085440 A1 | 4/2005 | Birch et al. |
| 2005/0118217 A1 | 6/2005 | Barnhart et al. |
| 2005/0147658 A1 | 7/2005 | Tapolsky et al. |
| 2005/0163830 A1 | 7/2005 | Rademacher et al. |
| 2005/0192309 A1 | 9/2005 | Palermo et al. |
| 2006/0210610 A1 | 9/2006 | Davidson et al. |
| 2006/0281775 A1 | 12/2006 | Kelly, II et al. |
| 2007/0065365 A1 | 3/2007 | Kugelmann et al. |
| 2007/0087036 A1 | 4/2007 | Durshlag et al. |
| 2007/0148097 A1 | 6/2007 | Finn et al. |
| 2008/0254105 A1 | 10/2008 | Tapolsky et al. |
| 2010/0015128 A1 | 1/2010 | Finn et al. |
| 2010/0015183 A1 | 1/2010 | Finn et al. |
| 2010/0087470 A1 | 4/2010 | Oksche et al. |
| 2011/0033541 A1 | 2/2011 | Myers et al. |
| 2011/0189259 A1 | 8/2011 | Vasisht et al. |
| 2011/0262522 A1 | 10/2011 | Finn et al. |
| 2013/0281481 A1 | 10/2013 | Myers et al. |
| 2014/0005218 A1 | 1/2014 | Myers et al. |
| 2014/0378497 A1 | 12/2014 | Myers et al. |
| 2015/0246005 A1 | 9/2015 | Myers et al. |
| 2016/0113885 A1 | 4/2016 | Myers et al. |

FOREIGN PATENT DOCUMENTS

| | | |
|---|---|---|
| DE | 2449865 B2 | 4/1976 |
| DE | 3630603 C2 | 3/1988 |
| EP | 0069600 A2 | 1/1983 |
| EP | 0 324 725 A1 | 7/1989 |
| EP | 0 324 725 B1 | 7/1989 |
| EP | 0219762 B1 | 12/1990 |
| EP | 0259749 B1 | 8/1991 |
| EP | 0200508 B1 | 10/1991 |
| EP | 0241178 B1 | 1/1992 |
| EP | 0273069 B1 | 10/1992 |
| EP | 0250187 B1 | 9/1993 |
| EP | 0452446 B1 | 12/1993 |
| EP | 0381194 B1 | 8/1994 |
| EP | 0440462 B1 | 12/1994 |
| EP | 0514691 B1 | 3/1996 |
| EP | 0598606 B1 | 6/1999 |
| EP | 0949925 B1 | 10/1999 |
| EP | 1110546 A1 | 6/2001 |
| EP | 1897543 A1 | 3/2008 |
| EP | 2461795 B1 | 1/2016 |
| GB | 2447016 A | 9/2008 |
| JP | 62126950 | 6/1987 |
| JP | 02265444 | 10/1990 |
| JP | 05147140 | 6/1993 |
| JP | 07322812 | 12/1995 |
| JP | 2001279100 | 10/2001 |
| WO | WO-91/05540 A1 | 5/1991 |
| WO | WO-92/15289 A1 | 9/1992 |
| WO | WO-95/05416 A2 | 2/1995 |
| WO | WO-95/18046 A1 | 7/1995 |
| WO | WO-96/26720 A1 | 9/1996 |
| WO | WO-98/17251 A1 | 4/1998 |
| WO | WO-99/17744 A1 | 4/1999 |
| WO | WO-99/44580 A1 | 9/1999 |
| WO | WO-99/55312 A2 | 11/1999 |
| WO | WO-00/18365 A2 | 4/2000 |
| WO | WO-00/42992 A2 | 7/2000 |
| WO | WO-00/51593 A2 | 9/2000 |
| WO | WO-00/51593 A3 | 9/2000 |
| WO | WO-01/70194 A1 | 9/2001 |
| WO | WO-01/91721 A2 | 12/2001 |
| WO | WO 03/003957 A1 | 1/2003 |
| WO | WO-03/030882 A1 | 4/2003 |
| WO | WO-03/030883 A1 | 4/2003 |
| WO | WO-2005/079750 A2 | 2/2004 |
| WO | WO-2005/079750 A3 | 2/2004 |
| WO | 2006089973 A2 | 8/2006 |
| WO | 2006089973 A3 | 12/2006 |
| WO | WO-2007/070632 A2 | 6/2007 |
| WO | WO-2008/002579 A2 | 1/2008 |
| WO | WO-2008/002579 A3 | 1/2008 |
| WO | WO-2008/011194 A2 | 1/2008 |
| WO | WO-2008/025791 A1 | 3/2008 |
| WO | WO-2008025791 A1 * | 3/2008 ............ A61P 25/04 |
| WO | WO-2008/040534 A2 | 4/2008 |
| WO | WO-2008/040534 A3 | 4/2008 |
| WO | WO-2008/068471 A1 | 6/2008 |
| WO | WO-2008/100434 A1 | 8/2008 |
| WO | WO-2008/104737 A1 | 9/2008 |
| WO | WO-2011/017483 A2 | 2/2011 |
| WO | WO-2011/017483 A3 | 2/2011 |

OTHER PUBLICATIONS

Avdeef, A. (2003). "Absorption and Drug Development: Solubility, Permeability, and Charge State," Wiley-Interscience, 8 pages.

Bettini, R. et al. (Feb. 23, 2001). "Translocation of drug particles in HPMC matrix gel layer: effect of drug solubility and influence on release rate," *J Control Release* 70(3):383-391.

Bodmeier, R. (1989). "Evaluation of Drug-Containing Poylmer Films Prepared from Aqueous Latexes," Pharmaceutical Research, vol. 6, No. 8, 1989.

Borsadia, S.B. et al. (May 2003). "Oral Film Technology," *Drug Delivery Technology* 3(3): 63-66.

Lazaridou et al., Thermophysical proprties of chitosan, chitosan-starch and chitosan-pullulan films near the glass Carbohydrate Polymers 48: 179-190 (2002).

Mahmood et al., "A limited sampling method for the estimation of AUC and Cmax of carbamazepine and carbamazepine epoxide following a single and multiple dose of a sustained-release product." BrJ Clin Pharmacol 1998; 45: pp. 241-246.

Notification of Transmittal of the International Search Report and the Written Opinion of the International Searching or the Declaration for International Application No. PCT/US2010/044488 dated Apr. 11, 2011.

Peh et al. (1999). "Polymeric films as vehicle for buccal delivery:swelling, mechanical, and bioadhesive properties," *J Pharmaceut Sci* (www.ualberta.ca/-csps) 2(2):53-61.

Repka et al., "Bioadhesive Properties of hydroxypropylcellulose topical films produced by hot melt extrusion," Journal Controlled Release, 70: 341-351 (2001).

Repka et al., "Influence of Vitamin E TPGS on the properties of hydrophilic films produced by hot melt extrusion", International Journal of Pharmaceutics 202(1-2): 63-70 (Jul. 20, 2000).

"Suboxone Subligualtabletten" In: Verlag Rote Liste Service GmbH: "ROTE LISTE 2008" 2008, Verlag Rote Liste GmbH, Frankfurt/Main, XP002624986, p. 39018, the whole document.

Written Opinion of the International Searching Authority for International Application No. PCT/US2010/044488 dated Apr. 2011, 4 pages.

Ansel, H.C. et al. (1999). "New Drug Development and Approval Process" Chapter 2 in *Pharmaceutical Dosage Forms and Drug Delivery Systems*, Seventh Edition, Balado, D. et al. eds., Lippincott Williams & Wilkins, 121 pages.

Brewster, D. et al. (Aug. 1981). "The systemic bioavailability of buprenorphine by various routes of administration," *J Pharm Pharmacol* 33(8):500-506.

Bullingham, R.E et al. (Nov. 1980). "Buprenorphine kinetics," *Clin Pharmacol Ther* 28(5):667-672.

Bullingham, R.E et al. (Aug. 1981). "Sublingual buprenorphine used postoperatively: clinical observations and preliminary pharmacokinetic analysis," *Br J Clin Pharmacol* 12(2):117-122.

(56) References Cited

OTHER PUBLICATIONS

Bullingham, R.E. et al. (May 1982). "Sublingual buprenorphine used postoperatively: ten hour plasma drug concentration analysis," *Br J Clin Pharmacol* 13(5):665-673.

Chamberlain, J.M. et al. (Nov. 1994). "A comprehensive review of naloxone for the emergency physician," *Am J Emerg Med* 12(6):65-660.

Chang, Y. et al. (Mar. 2006, e-published Dec. 28, 2005). "Novel metabolites of buprenorphine detected in human liver microsomes and human urine," *Drug Metab Dispos* 34(3):440-448.

Chiang, C.N. et al. (May 21, 2003). "Pharmacokinetics of the combination tablet of buprenorphine and naloxone," *Drug Alcohol Depend* 70(2 Suppl):S39-S47.

Elkader, A. et al. (2005). "Buprenorphine: clinical pharmacokinetics in the treatment of opioid dependence," *Clin Pharmacokinet* 44(7):661-680.

Fishman J. et al. (Dec. 1973). "Disposition of naloxone-7,8,3H in normal and narcotic-dependent men," *J Pharmacol Exp Ther* 187(3):575-580.

Gandhi, R.B. et al. (1994). "Oral cavity as a site for bioadhesive drug delivery," *Advanced Drug Delivery Reviews* 13:43-74.

Guo, J-H et al. (1997). "Water Soluble Film for Oral Administration," presented at The 24th International Symposium on Controlled Release of Bioactive Materials, Stockholm, Sweden, Jun. 15-19, 1997, 3 pages.

Harris, D.S. et al. (Dec. 22, 2000). "Buprenorphine and naloxone co-administration in opiate-dependent patients stabilized on sublingual buprenorphine," *Drug Alcohol Depend* 61(1):85-94.

Harris, D.S. et al. (2004). "Pharmacokinetics and subjective effects of sublingual buprenorphine, alone or in combination with naloxone: lack of dose proportionality," *Clin Pharmacokinet* 43(5):329-340.

Hogben, C.A.M. et al. (1958). "On the Mechanism of Intestinal Absorption of Drugs," *Journal of Pharmacology and Experimental Therapeutics* 125(4):275-282.

Iribarne, C. et al. (1997). "Involvement of cytochrome P450 3A4 in N-dealkylation of buprenorphine in human liver microsomes," *Life Sci* 60(22):1953-1964.

Kuhlman, J.J. Jr. et al. (Oct. 1996). "Human pharmacokinetics of intravenous, sublingual, and buccal buprenorphine," *J Anal Toxicol* 20(6):369-378.

Martin, W. et al. (1999). "Bioavailability Investigation of a New Tilidine/Naloxone Liquid Formulation Compared to a Reference Formulation," Arzneim-Forsch/Drug Res 49(II), NR 7, 10 pages.

McQuay, H. J. et al. (1995). "Buprenorphine Kinetics in Humans," in *Buprenorphine: Combatting Drug Abuse with a Unique Opioid* Cowan, A. et al. eds., Wiley-Liss, Inc., 13 pages.

Mendelson, J. et al. (Jan. 1997). "Bioavailability of sublingual buprenorphine," *J Clin Pharmacol* 37(1):31-37.

Nath, R.P. et al. (Jun. 1999). "Buprenorphine pharmacokinetics: relative bioavailability of sublingual tablet and liquid formulations," *J Clin Pharmacol* 39(6):619-623.

Robinson, S.E. (2002). "Buprenorphine: an analgesic with an expanding role in the treatment of opioid addiction," *CNS Drug Rev* 8(4):377-390.

Rowland, M. et al. (1995). "Why Clinical Pharmacokinetics?" Chapter 1 in *Clinical Pharmacokinetics Concepts and Applications*, Third Edition, Balado D. et al. eds., Lippincott Williams & Wilkins, 9 pages.

Rance, M.J. et al. (Sep. 1977). "The metabolism of phenolic opiates by rat intestine," *Xenobiotica* 7(9):529-536.

Rowland, M. et al. (1995). "Variability" Chapter 13 in *Clinical Pharmacokinetics Concepts and Applications*, Third Edition, Balado D. et al. eds., Lippincott Williams & Wilkins, 19 pages.

Rowland, M. et al. (2011). "Therapeutic Relevance" Chapter 1 in Clinical *Pharmacokinetics and Pharmacodynamics Concepts and Applications*, Fourth Edition, Lippincott Williams & Wilkins, 15 pages.

Sarkar, N. (1995). "Kinetics of thermal gelation of methylcellulose and hydroxypropylmethylcellulose in aqueous solutions," *Carbohydrate Polymers* 26(3):195-203.

Shargel, L. et al. (2005). "Physiologic Factors Related to Drug Absorption" Chapter 13 in *Applied Biopharmaceutics & Pharmacokinetics* Fifth Edition, The McGraw-Hill Companies,. Inc., 42 pages.

Shargel, L. et al. (2005). "Relationship Between Pharmacokinetics and Pharmacodynamics" Chapter 19 in *Applied Biopharmaceutics & Pharmacokinetics* Fifth Edition, The McGraw-Hill Companies, Inc., 39 pages.

Shojaei, A.H. (Jan.-Apr. 1998). "Buccal mucosa as a route for systemic drug delivery: a review," *J Pharm Pharm Sci* 1(1):15-30.

Smith, K. et al. (May 2012). "Low absolute bioavailability of oral naloxone in healthy subjects," *Int J Clin Pharmacol Ther* 50(5):360-367.

Strain, E.C. et al. (Apr. 9, 2004). "Relative bioavailability of different buprenorphine formulations under chronic dosing conditions," *Drug Alcohol Depend* 74(1):37-43.

Suboxone Sublingual Tablets US FDA Summary Basis of Approval, 48 pages.

Suboxone Sublingual Tablet US FDA Label Revised 2006, 4 pages.

Suboxone Sublingual Tablets Package Insert, Distributed by Reckitt Benckiser Pharmaceuticals Inc., 4 pages.

Suboxone Product Insert, (Apr. 2014), Distributed by Reckitt Benckiser Pharmaceuticals Inc., 24 pages.

Subutex Summary Product Insert (2013). Reckitt Benckiser Pharmaceuticals Limited, 11 pages.

European Medicines Agency Suboxone Tablets Summary of Product Characteristics, Jun. 25, 2009, 84 pages.

European Medicines Agency Suboxone Tablets Scientific Discussion Oct. 19, 2006, 42 pages.

Suboxone Sublingual Tablets US FDA Medical Review, Center for Drug Evaluation and Research, 35 pages.

Tam, Y.K. (Oct. 1993). "Individual variation in first-pass metabolism," *Clin Pharmacokinet* 25(4):300-328.

Walter, D.S. et al. (1995). *Buprenorphine: Combatting Drug Abuse with a Unique Opioid*, Cowan, A. et al. eds., Wiley-Liss, Inc., 25 pages.

Washington, T. et al. (2013). "Buprenorphine: Side Effects and Tolerability" Chapter 14 in *Handbook of Methadon Prescribing and Buprenorphine Therapy*, Cruciani, R.A. et al. eds, 11 pages.

Welsh, C. et al. (2005). "Buprenorphine: A (Relatively) New Treatment for Opioid Dependence," *Psychiatry* 11 pages.

Cassidy, J.P. et al. (1993). "Controlled buccal delivery buprenorphine," Journal of Controlled Release, 25:21-29.

Matharu, R.P. et al. (1992). "Development and Stability Assessment of Buprenorphine Sublingual Tablets for the Treatment of Opiate Addiction," *Pharmaceutical Research* PT6056, 2 pages.

Fudala, P.J. et al. (Mar. 1, 1998). "Effects of buprenorphine and naloxone in morphine-stabilized opioid addicts," *Drug Alcohol Depend* 50(1):1-8.

McAleer, S.D. et al. (Oct. 24, 2003). "Pharmacokinetics of high-dose buprenorphine following single administration of sublingual tablet formulations in opioid naïve healthy male volunteers under a naltrexone block," *Drug Alcohol Depend* 72(1):75-83.

Liang, A.C. et al. (2001). "Fast-dissolving intraoral drug delivery systems," *Expert Opin Ther Patents* 11(6):981-986.

Johnson, R.E. et al. (Mar. 2005). "Buprenorphine: considerations for pain management," *J Pain Symptom Manage* 29(3):297-326.

Merriam Webster Collegiate Dictionary, (2000). 10th edition, p. 458, 3 pages.

Stoller, K.B. et al. (Mar. 2001). "Effects of buprenorphine/naloxone in opioid-dependent humans," *Psychopharmacology* 154(3):230-242.

Lachman, L. et al. (1986). "Sustained Release Dosage Forms," Chapter 14 in *The Theory and Practice of Industrial Pharmacy*, Third Edition, Lea & Febiger, Philadelphia, pp. 430-434.

Merriam Webster Collegiate Dictionary, (2000). 10th edition, p. 616, 3 pages.

Lewis, J.W. et al. (May 1970). "Novel analgetics and molecular rearrangements in the morphine-thebaine group. 18. 3-deoxy-6,14-endo-etheno-6,7,8,14-tetrahydrooripavines," *J Med Chem* 13(3):525-527.

Shore, P.A.. et al. (1957). "The Gastric Secretion of Drugs: A pH Partition Hypothesis," pp. 361-369.

(56) References Cited

OTHER PUBLICATIONS

Swarbrick, J. et al. ed. (2002). "Drug Delivery-Buccal Route," in *Encyclopedia of Pharmaceutical Technology*, Second Edition, vol. 1, pp. 800-809.
U.S. FDA Guidance for Industry Bioavailability and Bioequivalence Studies for Orally Administered Drug Products—General Considerations (Mar. 2003), 26 pages.
Dawson, R.M.C. et al. (1986). *Data for Biochemical Research*, Third Edition, Oxford Science Publications, 12 pages.
Voet, M.A. ed. (2008). Hierarchy of Patents, Pharmaceutical, Biological and Medical Device Patents, *The Generic Challenge*. Brown Walker Press, 7 pages.
Campbell, N.D. et al. (Feb. 2012, e-published Jan. 18, 2012). "The history of the development of buprenorphine as an addiction therapeutic," *Ann NY Acad Sci* 1248:124-139.
Ciraulo, D.A. et al. (2006). "Pharmacokinetics and Pharmacodynamics of Multpiple Sublingual Buprenorphine Tablets in Dose-Escalation Trials," *J Clin Pharmacol* 46:179-192.
Opposition to European U.S. Pat. No. 2 461 795, 36 pages. (with English Translation).
Reply to Notice of Opposition to European U.S. Pat. No. 2461795 filed Apr. 5, 2017, 71 pages.
*Dr. Reddy's Laboratories, Inc.* Vs. *Indivior UK Limited* USPTO, IPR2016-01113, U.S. Pat. No. 8,475,832.
*Teva Pharmaceuticals Usa, Inc.* Vs. *Indivior UK Limited*, USPTO, IPR2016-00280, U.S. Pat. No. 8,475,832.
*Biodelivery Sciences International, Inc.* V. *Reckitt Benckiser Pharmaceuticals, Inc.* IPR2014-00325, U.S. Pat. No. 8,475,832.
*Biodelivery Sciences International, Inc.* V. *Reckitt Benckiser Pharmaceuticals, Inc.*, IPR2014-00998, U.S. Pat. No. 8,475,832.
IPR2014-00998: Decision Denying Institution of Inter Partes Review and Dismissing Motion for Joinder Decision, Patent 8,475,832B2, *BioDelivery Sciences International, Inc.* v. *RB Pharmaceuticals Limited*, entered Dec. 19, 2014, 10 pages.
Decision Denying Institution of Inter Partes Review dated Dec. 2, 2016, Case IPR2016-01113, Patent 8,475,83262, 20 pages.
Decision Denying Institution of Inter Partes Review, *Teva Pharmaceuticals Usa, Inc.* Vs. *Indivior UK Limited*, CASe IPR2016-00280, U.S. Pat. No. 8,475,832 B2, Jun. 10, 2016, 20 pages.
Petition for Inter Partes Review of U.S. Pat. No. 8,475,832, IPR2016-01113, *Dr. Reddy's Laboratories, LTD. and Dr. Reddy's Laboratories, Inc.* Vs. *Indivior UK Limited*, May 31, 2016, 58 pages.
Petition for Inter Partes Review of U.S. Pat. No. 8,475,832, *BioDelivery Sciences International, Inc.* Vs. *RB Pharmaceuticals Limited*, Jun. 20, 2014, 62 pages.
*Indivior Inc. Et Al* V. *Teva Pharmaceuticals Usa, Inc.*, US District Court of Delaware, Case 1:16cv178.
Patent Owner Indivior UK Limited's Preliminary Response, *Teva Pharmaceuticals Usa, Inc.* Vs. *Indivior UK Limited*, Mar. 15, 2016, U.S. Pat. No. 8,475,832, Case No. IPR2016-00280, 56 pages.
Final Written Decision, *BioDelivery Sciences International, Inc.* vs. *RB Pharmaceuticals Limited*, Case IPR2014-00325, U.S. Pat. No. 8,475,832B2, Jun. 30, 2015, 28 pages.
Petition for Inter Partes Review *Teva Pharmaceuticals USA, Inc.* v. *RB Pharmaceuticals LTD.* U.S. Pat. No. 8,475,832, Dec. 3, 2015, 54 pages.
Patent Owner Preliminary Response, *BioDelivery Sciences International, Inc.* Vs. *RB Pharmaceuticals Limited*, Case IPR2014-00998, U.S. Pat. No. 8,475,832, Oct. 1, 2014, 56 pages.
*Fuisz* V. *Teva Pharmaceuticals Usa, Inc. et al.*, US District Court of Florida Southern District, Case 1:16mc21017.
*Indivior Inc. Et Al* V. *Sandoz Inc.*, US-DIS-DED, 1:15cv1051.
*Indivior Inc. Et Al* V. *Mylan Technologies Inc. Et Al.*, US-DIS-WVND, 1:15cv209.
*Indivior Inc. Et Al* V. *Mylan Technologies Inc. Et Al*, US-DIS-DED, 1:15cv1016.
*Reckitt Benckiser Pharmaceuticals Inc. Et Al* V. *Alvogen Pine Brook Inc.*, US-DIS-DED, 1:15cv477.
*Reckitt Benckiser Pharmaceuticals Inc. Et Al* V. *Par Pharmaceutical Inc. Et Al*, US-DIS-DED, 1:14cv1573.
*Reckitt Benckiser Pharmaceuticals Inc. Et Al* V. *Watson Laboratories Inc. Et Al.*, US-DIS-DED, 1:14cv1574.
*Reckitt Benckiser Pharmaceuticals Inc. Et Al* V. *Teva Pharmaceuticals USA Inc.*, US-DIS-DED, 1:14cv1451.
*Biodelivery Sciences International, Inc.* V. *Reckitt Benckiser Pharmaceuticals, Inc. Et Al.*, US-DIS-NCED, 5:14cv529.
*BioDelivery Sciences International, Inc.* Vs. *RB Pharmaceuticals Limited*, US PTO ALE, IPR2014-00998.
*Reckitt Benckiser Pharmaceuticals Inc. Et Al* V. *Par Pharmaceutical Inc. Et Al*, US-DIS-DED, 1:14cv422.
*BioDelivery Sciences International, Inc.* Vs. *RB Pharmaceuticals Limited*, US PTO ALE, IPR2014-00325.
*Reckitt Benckiser Pharmaceuticals Inc. Et Al* V. *Alvogen Pine Brook Inc.*, US-DIS-DED, 1:13cv2003.
*Reckitt Benckiser Pharmaceuticals, Inc. Et Al* V. *Biodelivery Sciences International, Inc.*, US-DIS-NCED, 5:13cv760.
*Reckitt Benckiser Pharmaceuticals Inc. Et Al* V. *Watson Laboratories Inc., Et Al.*, US-DIS-DED, 1:13cv1674.
*Reckitt Benckiser Pharmaceuticals Inc. Et Al* V. *Par Pharmaceutical Inc. Et Al*, US-DIS-DED, 1:13cv1461.
Consent Decree and Final Judgement Regarding U.S. Pat. No. 8,475,832, dated Dec. 16, 2016, *Indivior Inc.* v. *Mylan Technologies Inc.*, C.A. No. 15-Cv-01016 RGA, 3 pages.
Trial Opinion of Jun. 3, 2016, for *Reckitt Benckiser Pharmaceuticals, Inc. et al* v. *Watson Laboratories, Inc. et al*, US District Court for the District of Delaware, Civil Action No. 13-1674-RGA and Civil Action No. 14-422-RGA, 61 pages.
*Dr. Reddy's Laboratories S.A. et al.* v. *Indivior UK Limited*, Petition for Inter Partes Review of U.S. Pat. No. 9,687,454, Case No. IPR2019-00328, filed Nov. 13, 2018, 76 pages.
*Dr. Reddy's Laboratories S.A. et al.* v. *Indivior UK Limited*, Petition for Inter Partes Review of U.S. Pat. No. 9,687,454, Case No. IPR2019-00329, filed Nov. 13, 2018, 49 pages.
Suboxone® tablet label approved by the FDA Oct. 8, 2002, 49 pages.
Aframian et al, "The distribution of oral mucosal pH values in healthy saliva secretors," Oral Dis., 12(4):420-423 (2006).
Doherty et al, "Microenvironment pH control of drug dissolution," International Journal of Pharmaceutics, 50:223-232 (1989).
Florence et al, Physiochemical Principles of Pharmacy, 2nd Edition, Chapter 3, pp. 47-80 (1988).
Weinberg et al, "Sublingual absorption of selected opioid analgesics," Clin Pharmacol Ther, 44(3):335-342 (1988).
Yosipovitch et al, "Distribution of Mucosal pH on the Bucca, Tongue, Lips and Palate," Acta Derm Venereol, 81:178-180 (2001).
Complaint, *Par Pharmaceuticals, Inc.* v. *Indivior Inc and Indivior UK Limited*, US District Court for the Eastern District of Virginia, Richmond Division, Nov. 13, 2017 (28 pages).
Satyabrata et al, "Design and In Vitro Evaluation of Mucoadhesive Buccal Tablets of Perindopril Prepared by Sintering Technique," Asian Journal of Pharmaceutical and Clinical Research, 3(4):4-10 (2010).
Bottenberg et al, "Development and Testing of Bioadhesive, Fluoride-containing Slow-release Tablets for Oral Use," J. Pharm. Pharmacol., 43:457-464 (1991).
European Patent Office Preliminary Opinion on Opposition in European Patent No. 2 461 795 (Sep. 19, 2017).
*Indivior Inc. et al.* v. *Actavis Laboratories UT Inc.*, 2:17-cv-01034 (D. Utah), Filing Date: Sep. 14, 2017.
*Indivior Inc. et al.* v. *Alvogen Pine Brook, Inc.*, 2:17-cv-07106 (D.N.J.), Filing Date: Sep. 14, 2017.
*Indivior Inc. et al.* v. *Dr. Reddy's Laboratories S.A. et al.*, 2:17-cv-07111 (D.N.J.), Filing Date: Sep. 14, 2017.
*Indivior Inc. et al.* v. *Teva Pharmaceuticals USA, Inc.*, 2:17-cv-07115 (D.N.J.), Filing Date: Sep. 14, 2017.
*Indivior Inc. et al.* v. *Par Pharmaceutical Inc. et al.*, 2:17-cv-07997 (D.N.J.), Filing Date: Oct. 6, 2017.
*Indivior Inc. et al.* v. *Mylan Technologies, Inc. et al.*, 1:17-cv-00157 (N.D.W.Va.), Filing Date: Sep. 14, 2017 (Dismissed).
*Indivior Inc. et al.* v. *Par Pharmaceutical Inc.*, 7:17-cv-07020 (S.D.N.Y.), Filing Date: Sep. 14, 2017 (Dismissed).
*Indivior Inc.* v. *Actavis Laboratories UT, Inc.*, No. 1:18-cv-00499 (D. Del.).

(56) References Cited

OTHER PUBLICATIONS

Affidavit of Christopher Butler dated Oct. 2, 2018, http://web.archive.org/web/20060206134214/http://www.fda.gov:80/cder/iig/IIGZIP.EXE, 411 pages.
Physicians' Desk Reference (2004). 58th Edition, 6 pages.
*Dr. Reddy's Laboratories S.A. et al.* v. *Indivior UK Limited*, Decision Denying Institution of Inter Partes Review, U.S. Pat. No. 9,687,454, Case No. IPR2019-00328, filed Jun. 3, 2019, 21 pages.
*Dr. Reddy's Laboratories S.A. et al.* v. *Indivior UK Limited*, Corrected Declaration of Nandita Das, Ph.D, U.S. Pat. No. 9,687,454, Case No. IPR2019-00328, filed Mar. 26, 2019, 69 pages.
*Dr. Reddy's Laboratories S.A. et al.* v. *Indivior UK Limited*, Institution of Inter Partes Review, U.S. Pat. No. 9,687,454, Case No. IPR2019-00329, filed Jun. 3, 2019, 29 pages.
"Bioequivalence" and "Bioequivalent" 2014. Merriam Webster (www.m-w.com).
Strain et al., "Blockade of hydromorphone effects by buprenorphine/naloxone and buprenorphine," Psychopharmacology, vol. 159, pp. 161-166 (2002).

\* cited by examiner

SUBLINGUAL AND BUCCAL FILM COMPOSITIONS

CROSS-REFERENCE TO RELATED APPLICATIONS

This application is a continuation of U.S. application Ser. No. 15/483,769 filed Apr. 10, 2017, which is a continuation of U.S. application Ser. No. 14/989,669 filed Jan. 6, 2016, issued as U.S. Pat. No. 9,687,454, which is a continuation of U.S. application Ser. No. 14/715,462 filed May 18, 2015, abandoned, which is a continuation of U.S. application Ser. No. 14/478,786 filed Sep. 5, 2014, abandoned, which is a continuation of U.S. application Ser. No. 13/964,975, filed Aug. 12, 2013, abandoned, which is a continuation of U.S. application Ser. No. 13/923,749 filed Jun. 21, 2013, abandoned, which is a continuation of U.S. application Ser. No. 12/537,571 filed Aug. 7, 2009, issued as U.S. Pat. No. 8,475,832.

FIELD OF THE INVENTION

The present invention relates to compositions, methods of manufacture, products and methods of use relating to films containing therapeutic actives. The invention more particularly relates to self-supporting film dosage forms which provide a therapeutically effective dosage, essentially matching that of currently-marketed tablets containing the same active. Such compositions are particularly useful for treating narcotic dependence while providing sufficient buccal adhesion of the dosage form.

BACKGROUND OF THE RELATED TECHNOLOGY

Oral administration of two therapeutic actives in a single dosage form can be complex if the intention is to have one active absorbed into the body and the other active remain substantially unabsorbed. For example, one active may be relatively soluble in the mouth at one pH, and the other active may be relatively insoluble at the same pH. Moreover, the absorption kinetics of each therapeutic agent may be substantially different due to differing absorption of the charged and uncharged species. These factors represent some of the challenges in appropriately co-administering therapeutic agents.

Co-administration of therapeutic agents has many applications. Among such areas of treatment include treating individuals who suffer from narcotic dependence. Such individuals have a tendency to suffer from serious physical dependence on the narcotic, resulting in potentially dangerous withdrawal effects when the narcotic is not administered to the individual. In order to help individuals addicted to narcotics, it is known to provide a reduced level of a drug, which provides an effect of satisfying the body's urge for the narcotic, but does not provide the "high" that is provided by the misuse of the narcotic. The drug provided may be an agonist or a partial agonist, which provides a reduced sensation and may help lower dependence on the drug. However, even though these drugs provide only a low level of euphoric effect, they are capable of being abused by the individuals parenterally. In such cases, it is desirable to provide a combination of the drug with a second drug, which may decrease the likelihood of diversion and abuse of the first drug. For example, it is known to provide a dosage of an antagonist in combination with the agonist or partial agonist. The narcotic antagonist binds to a receptor in the brain to block the receptor, thus reducing the effect of the agonist.

One such combination of drugs has been marketed under the trade name Suboxone® as an orally ingestible tablet. However, such combinations in tablet form have the potential for abuse. In some instances, the patient who has been provided the drug may store the tablet in his mouth without swallowing the tablet, then later extract the agonist from the tablet and inject the drug into an individual's body. Although certain antagonists (such as highly water-soluble antagonists) may be used to help reduce the ability to separate the agonist, the potential for abuse still exists. It is desired to provide a dosage that cannot be easily removed from the mouth once it has been administered.

There is currently a need for an orally dissolvable film dosage form that provides the desired absorption levels of the agonist and antagonist, while providing an adhesive effect in the mouth, rendering it difficult to remove once placed in the mouth, thereby making abuse of the agonist difficult.

SUMMARY OF THE INVENTION

In one embodiment of the present invention, there is provided a film dosage composition including: a polymeric carrier matrix; a therapeutically effective amount of buprenorphine or a pharmaceutically acceptable salt thereof; a therapeutically effective amount of naloxone or a pharmaceutically acceptable salt thereof; and a buffer in an amount to provide a pH of the composition of a value sufficient to optimize absorption of the buprenorphine.

In another embodiment of the present invention, there is provided a film dosage composition including: a polymeric carrier matrix; a therapeutically effective amount of buprenorphine or a pharmaceutically acceptable salt thereof; a therapeutically effective amount of naloxone or a pharmaceutically acceptable salt thereof; and a buffer in an amount sufficient to inhibit the absorption of the naloxone when administered orally.

In still other embodiments, there may be provided a film dosage composition including: a polymeric carrier matrix; a therapeutically effective amount of buprenorphine or a pharmaceutically acceptable salt thereof; a therapeutically effective amount of naloxone or a pharmaceutically acceptable salt thereof; and a buffering system; where the buffering system includes a buffer capacity sufficient to maintain the ionization of naloxone during the time which the composition is in the oral cavity of a user.

In another embodiment of the invention, there is provided a method of treating narcotic dependence of a user, including the steps of: providing a composition including: a polymeric carrier matrix; a therapeutically effective amount of buprenorphine or a pharmaceutically acceptable salt thereof; a therapeutically effective amount of naloxone or a pharmaceutically acceptable salt thereof; and a buffer in an amount to provide a pH of the composition of a value sufficient to optimize absorption of the buprenorphine; and administering the composition to the oral cavity of a user.

In still another embodiment of the invention, there is provided a process of forming a film dosage composition including the steps of: casting a film-forming composition, the film-forming composition including: a polymeric carrier matrix; a therapeutically effective amount of buprenorphine or a pharmaceutically acceptable salt thereof; a therapeutically effective amount of naloxone or a pharmaceutically acceptable salt thereof; and a buffer in an amount to provide a pH of the composition of a value sufficient to optimize absorption of the buprenorphine and drying the film-forming composition to form a self-supporting film dosage composition.

In another embodiment, there is provided a film dosage composition including a therapeutically sufficient amount of buprenorphine or a pharmaceutically acceptable salt thereof and a therapeutically sufficient amount of naloxone or a pharmaceutically acceptable salt thereof, the film dosage composition having a bioequivalent release profile as compared to a Suboxone® tablet containing about 2 times the amount of buprenorphine or a pharmaceutically acceptable salt thereof.

Still other embodiments of the present invention provide an orally dissolving film formulation including buprenorphine and naloxone, where the formulation provides an in-vivo plasma profile having a Cmax of between about 0.624 ng/ml and about 5.638 ng/ml for buprenorphine and an in-vivo plasma profile having a Cmax of between about 41.04 pg/ml to about 323.75 pg/ml for naloxone.

DETAILED DESCRIPTION OF THE PREFERRED EMBODIMENTS

Definitions

As used herein, the term Cmax refers to the mean maximum plasma concentration after administration of the composition to a human subject. As also used herein, the term AUC refers to the mean area under the plasma concentration-time curve value after administration of the compositions formed herein. As will be set forth in more detail below, the term "optimizing the absorption" does not refer to reaching the maximum absorption of the composition, and rather refers to reaching the optimum level of absorption at a pH of about 2 to about 4. The "optimum" absorption may be, for example, a level that provides a bioequivalent absorption as administration of the currently available Suboxone® tablet. An "optimum" Cmax of buprenorphine is about 0.67 to about 5.36 mg/ml at dosages of from 2-16 mg buprenorphine at a given pH. Similarly, an "optimum" AUC of buprenorphine may be about 7.43 to about 59.46 hr*ng/ml at dosages of from 2-16 mg buprenorphine at a given pH. As will be described in more detail below, it has been surprisingly discovered that the absorption of one particular agonist, buprenorphine, can provide an optimum absorption at a pH of about 2-4 as well as about 5.5-6.5. Thus, one may "optimize" the absorption of buprenorphine by providing a pH of about 2-4 or about 5.5-6.5.

"Maximizing the absorption" refers to the maximum in vivo absorption values achieved at a pH of about 4 to about 9.

The term "local pH" refers to the pH of the region of the carrier matrix immediately surrounding the active agent as the matrix hydrates and/or dissolves, for example, in the mouth of the user.

By "inhibiting" the absorption of an active, it is meant achieving as complete an ionization state of the active as possible, such that little to none of the active is measurably absorbable. For example, at a pH of 3-3.5, the Cmax of an active such as naloxone for dosage of 0.5 mg to 4.0 mg ranges from 32.5 to 260 pg/ml, and an AUC of naloxone for dosage of 0.5 mg to 4.0 mg ranges from 90.55 to 724.4 hr*pg/ml. It is understood that at a pH lower than 3.0, further ionization would be expected and thus result in lower absorption.

The term "bioequivalent" means obtaining 80% to 125% of the Cmax and AUC values for a given active in a different product. For example, assuming Cmax and AUC values of buprenorphine for a commercially-available Suboxone® tablet (containing 2 mg buprenorphine and 0.5 mg naloxone) are 0.780 ng/ml and 6.789 hr*ng/ml, respectively, a bioequivalent product would have a Cmax of buprenorphine in the range of 0.624-0.975 ng/ml, and an AUC value of buprenorphine of 5.431-8.486 hr*ng/ml.

It will be understood that the term "film" includes thin films and sheets, in any shape, including rectangular, square, or other desired shape. The films described herein may be any desired thickness and size such that it may be placed into the oral cavity of the user. For example, the films may have a relatively thin thickness of from about 0.1 to about 10 mils, or they may have a somewhat thicker thickness of from about 10 to about 30 mils. For some films, the thickness may be even larger, i.e., greater than about 30 mils. Films may be in a single layer or they may be multi-layered, including laminated films.

Oral dissolving films generally fall into three main classes: fast dissolving, moderate dissolving and slow dissolving. Fast dissolving films generally dissolve in about 1 second to about 30 seconds in the mouth. Moderate dissolving films generally dissolve in about 1 to about 30 minutes in the mouth, and slow dissolving films generally dissolve in more than 30 minutes in the mouth. Fast dissolving films may consist of low molecular weight hydrophilic polymers (i.e., polymers having a molecular weight between about 1,000 to 9,000, or polymers having a molecular weight up to 200,000). In contrast, slow dissolving films generally have high molecular weight polymers (i.e., having a molecular weight in the millions).

Moderate dissolving films tend to fall in between the fast and slow dissolving films. Moderate dissolving films dissolve rather quickly, but also have a good level of mucoadhesion. Moderate dissolving films are also flexible, quickly wettable, and are typically non-irritating to the user. For the instant invention, it is preferable to use films that fall between the categories of fast dissolving and moderate dissolving. Such moderate dissolving films provide a quick enough dissolution rate, most desirably between about 1 minute and about 20 minutes, while providing an acceptable mucoadhesion level such that the film is not easily removable once it is placed in the oral cavity of the user.

Inventive films described herein may include one or more agonists or partial agonists used for the treatment of drug addiction. As used herein, the term "agonist" refers to a chemical substance that is capable of providing a physiological response or activity in the body of the user. The films described herein may further include one or more antagonists. As used herein, the term "antagonist" refers to any chemical substance that acts within the body of the user to reduce the physiological activity of another chemical substance. In some embodiments, an antagonist used herein may act to reduce and/or block the physiological activity of the agonist. The actives may be water-soluble, or they may be water-insoluble. As used herein, the term "water-soluble" refers to substances that are at least partially dissolvable in a solvent, including but not limited to water. The term "water-soluble" does not necessarily mean that the substance is 100% dissolvable in the solvent. The term "water-insoluble" refers to substances that are not dissolvable in a solvent, including but not limited to water. Solvents may include water, or alternatively may include other polar solvents by themselves or in combination with water.

Inventive Films

The present invention relates to methods of treating narcotic dependence in an individual. More desirably, the invention relates to the treatment of opioid dependence in an individual, while using a formulation and delivery that hinders misuse of the narcotic. Currently, treatment of opioid dependence is aided by administration of Suboxone®, which is an orally dissolvable tablet. This tablet which provides a combination of buprenorphine (an opioid agonist) and naloxone (an opioid antagonist). Therefore, the present invention provides a method of treating narcotic dependence by providing an orally dissolvable film dosage, which provides a bioequivalent effect to Suboxone®. The film dosage preferably provides buccal adhesion while it is in the user's mouth, rendering it difficult to remove after placement.

The film dosage composition preferably includes a polymeric carrier matrix. Any desired polymeric carrier matrix may be used, provided that it is orally dissolvable. Desirably, the dosage should have enough bioadhesion to not be easily removed and it should form a gel like structure when administered. The orally consumable films are preferably moderate-dissolving in the oral cavity and particularly suitable for delivery of actives, although both fast and sustained release compositions are also among the various embodiments contemplated.

The films used in the pharmaceutical products may be produced by a combination of at least one polymer and a solvent, optionally including other fillers known in the art. The solvent may be water, a polar organic solvent including, but not limited to, ethanol, isopropanol, acetone, or any combination thereof. In some embodiments, the solvent may be a non-polar organic solvent, such as methylene chloride. The film may be prepared by utilizing a selected casting or deposition method and a controlled drying process. For example, the film may be prepared through controlled drying processes, which include application of heat and/or radiation energy to the wet film matrix to form a viscoelastic structure, thereby controlling the uniformity of content of the film. Such processes are described in more detail in commonly assigned U.S. application Ser. No. 10/074,272, filed on Feb. 14, 2002, and published as U.S. Patent Publication No. 2003/0107149 A1, the contents of which are incorporated herein by reference in their entirety. Alternatively, the films may be extruded as described in commonly assigned U.S. application Ser. No. 10/856,176, filed on May 28, 2004, and published as U.S. Patent Publication No. 2005/0037055 A1, the contents of which are incorporated herein by reference in their entirety.

The polymer included in the films may be water-soluble, water-swellable, water-insoluble, or a combination of one or more either water-soluble, water-swellable or water-insoluble polymers. The polymer may include cellulose or a cellulose derivative. Specific examples of useful water-soluble polymers include, but are not limited to, polyethylene oxide, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water-insoluble polymers include, but are not limited to, ethyl cellulose, hydroxypropyl ethyl cellulose, cellulose acetate phthalate, hydroxypropyl methyl cellulose phthalate and combinations thereof. For higher dosages, it may be desirable to incorporate a polymer that provides a high level of viscosity as compared to lower dosages.

As used herein the phrase "water-soluble polymer" and variants thereof refer to a polymer that is at least partially soluble in water, and desirably fully or predominantly soluble in water, or absorbs water. Polymers that absorb water are often referred to as being water-swellable polymers. The materials useful with the present invention may be water-soluble or water-swellable at room temperature and other temperatures, such as temperatures exceeding room temperature. Moreover, the materials may be water-soluble or water-swellable at pressures less than atmospheric pressure. Desirably, the water-soluble polymers are water-soluble or water-swellable having at least 20 percent by weight water uptake. Water-swellable polymers having a 25 or greater percent by weight water uptake are also useful. In some embodiments, films formed from such water-soluble polymers may be sufficiently water-soluble to be dissolvable upon contact with bodily fluids.

Other polymers useful for incorporation into the films include biodegradable polymers, copolymers, block polymers and combinations thereof. It is understood that the term "biodegradable" is intended to include materials that chemically degrade, as opposed to materials that physically break apart (i.e., bioerodable materials). Among the known useful polymers or polymer classes which meet the above criteria are: poly(glycolic acid) (PGA), poly(lactic acid) (PLA), polydioxanes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly (lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°–347° F. (170°–175° C.); lactide/glycolide 100 L, believed to be 100% glycolide having a melting point within the range of 437°–455° F. (225°–235° C.); lactide/glycolide 85/15, believed to be 85% lactide and 15% glycolide with a melting point within the range of 338°–347° F. (170°–175° C.); and lactide/glycolide 50/50, believed to be a copolymer of 50% lactide and 50% glycolide with a melting point within the range of 338°–347° F. (170°–175° C.).

The Biodel materials represent a family of various polyanhydrides which differ chemically.

Although a variety of different polymers may be used, it is desired to select polymers that provide mucoadhesive properties to the film, as well as a desired dissolution and/or disintegration rate. In particular, the time period for which it is desired to maintain the film in contact with the mucosal tissue depends on the type of active contained in the composition. Some actives may only require a few minutes for delivery through the mucosal tissue, whereas other actives may require up to several hours or even longer. Accordingly, in some embodiments, one or more water-soluble polymers, as described above, may be used to form the film. In other embodiments, however, it may be desirable to use combinations of water-soluble polymers and polymers that are water-swellable, water-insoluble and/or biodegradable, as provided above. The inclusion of one or more polymers that are water-swellable, water-insoluble and/or biodegradable may provide films with slower dissolution or disintegration rates than films formed from water-soluble polymers alone. As such, the film may adhere to the mucosal tissue for longer periods or time, such as up to several hours, which may be desirable for delivery of certain active components.

Desirably, the individual film dosage has a small size, which is between about 0.5-1 inch by about 0.5-1 inch. Most preferably, the film dosage is about 0.75 inches×0.5 inches. The film dosage should have good adhesion when placed in the buccal cavity or in the sublingual region of the user. Further, the film dosage should disperse and dissolve at a moderate rate, most desirably dispersing within about 1 minute and dissolving within about 3 minutes. In some embodiments the film dosage may be capable of dispersing and dissolving at a rate of between about 1 to about 1.5 minutes.

For instance, in some embodiments, the films may include polyethylene oxide alone or in combination with a second polymer component. The second polymer may be another water-soluble polymer, a water-swellable polymer, a water-insoluble polymer, a biodegradable polymer or any combination thereof. Suitable water-soluble polymers include, without limitation, any of those provided above. In some embodiments, the water-soluble polymer may include hydrophilic cellulosic polymers, such as hydroxypropyl cellulose and/or hydroxypropylmethyl cellulose. In accordance with some embodiments, polyethylene oxide may range from about 20% to 100% by weight in the polymer component, more specifically about 30% to about 70% by weight, and even more specifically about 40% to about 60% by weight. In some embodiments, one or more water-swellable, water-insoluble and/or biodegradable polymers also may be included in the polyethylene oxide-based film. Any of the water-swellable, water-insoluble or biodegradable polymers provided above may be employed. The second polymer component may be employed in amounts of about 0% to about 80% by weight in the polymer component, more specifically about 30% to about 70% by weight, and even more specifically about 40% to about 60% by weight.

The molecular weight of the polyethylene oxide also may be varied. In some embodiments, high molecular weight polyethylene oxide, such as about 4 million, may be desired to increase mucoadhesivity of the film. In some other embodiments, the molecular weight may range from about 100,000 to 900,000, more specifically from about 100,000 to 600,000, and even more specifically from about 100,000 to 300,000. In some embodiments, it may be desirable to combine high molecular weight (600,000 to 900,000) with low molecular weight (100,000 to 300,000) polyethylene oxide in the polymer component.

A variety of optional components and fillers also may be added to the films. These may include, without limitation: surfactants; plasticizers; polyalcohols; anti-foaming agents, such as silicone-containing compounds, which promote a smoother film surface by releasing oxygen from the film; thermo-setting gels such as pectin, carageenan, and gelatin, which help in maintaining the dispersion of components; inclusion compounds, such as cyclodextrins and caged molecules; coloring agents; and flavors. In some embodiments, more than one active components may be included in the film.

Additives may be included in the films. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all film components.

Further additives may flow agents and opacifiers, such as the oxides of magnesium aluminum, silicon, titanium, etc. desirably in a concentration range of about 0.02% to about 3% by weight and desirably about 0.02% to about 1% based on the weight of all film components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the texture properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total film composition.

It further may be useful to add silicon dioxide, calcium silicate, or titanium dioxide in a concentration of about 0.02% to about 1% by weight of the total composition. These compounds act as flow agents and opacifiers.

Lecithin is one surface active agent for use in the films described herein. Lecithin may be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

Suitable coloring agents include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

Anti-foaming and/or de-foaming components may also be used with the films. These components aid in the removal of air, such as entrapped air, from the film-forming compositions. Such entrapped air may lead to non-uniform films. Simethicone is one particularly useful anti-foaming and/or de-foaming agent. The present invention, however, is not so limited and other anti-foam and/or de-foaming agents may suitable be used.

As a related matter, simethicone and related agents may be employed for densification purposes. More specifically, such agents may facilitate the removal of voids, air, moisture, and similar undesired components, thereby providing denser, and thus more uniform films. Agents or components which perform this function can be referred to as densification or densifying agents. As described above, entrapped air or undesired components may lead to non-uniform films.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Any other optional components described in commonly assigned U.S. Pat. No. 7,425,292 and U.S. application Ser. No. 10/856,176, referred to above, also may be included in the films described herein.

When the dosage form includes at least one antagonist, it may be desired to control the release of the antagonist, so as to delay or wholly prevent the release of the antagonist from the dosage when taken orally. Desirably, the dosage form is a self-supporting film composition, which is placed into the oral cavity of the user. In a dosage form that is to be placed in the oral cavity, it is desired to absorb the agonist buccally, so as to provide rapid integration of the agonist into the body of the user. At the same time, it may be desired to prevent or reduce absorption of any antagonist buccally, thereby allowing the antagonist to be swallowed and destroyed in the stomach. Reducing the absorption of an antagonist may be achieved via physical means, such as by encapsulating the antagonist in a material that blocks absorption. It is desired, however, to reduce the absorption of the antagonist by chemical means, such as by controlling the local pH of the dosage.

It has been found that by controlling the local pH of the dosage form, the release and/or absorption of the actives therein may be controlled. For example, in a dosage that includes an amount of an agonist, the local pH may be controlled to a level that maximizes its release and/or absorption into the oral cavity of the user. In dosages incorporating an amount of an agonist and an amount of an antagonist, the local pH may be controlled to a level that maximizes the release and/or absorption of the agonist while simultaneously minimizing the release and/or absorption of the antagonist.

The dosage form preferably includes a combination of a partial agonist and an antagonist, while the dosage has a controlled pH. In one embodiment, the partial agonist may include buprenorphine or a pharmaceutically acceptable salt thereof, while the antagonist includes naloxone or a therapeutically acceptable salt thereof. It should be understood that the present invention is not limited to the use of buprenorphine and naloxone, and any agonist (or partial agonist) and any antagonist may be incorporated into the present invention for use in treatment of drug addiction. The agonist and optional antagonist should be selected from those agonists and antagonists that are useful in treating the particular narcotic dependence being treated.

As discussed above, the local pH of the dosage is preferably controlled to provide the desired release and/or absorption of the agonist and antagonist. Buprenorphine is known to have a pKa of about 8.42, while naloxone has a pKa of about 7.94. According to pH partition theory, one would expect that saliva (which has a pH of about 6.5) would maximize the absorption of both actives. However, it has been surprisingly discovered by the Applicants that by buffering the dosage to a particular pH level, the optimum levels of absorption of the agonist and antagonist may be achieved. Desirably, the local pH of a composition including an agonist and an antagonist is between about 2 to about 4, and most desirably is from 3 to 4. At this local pH level, the optimum absorption of the agonist and the antagonist is achieved. As will be described in more detail in the Examples below, controlling the local pH of the film compositions of the present invention provides a system in which the desired release and/or absorption of the components is bioequivalent to that of a similar Suboxone® tablet.

In one embodiment, the dosage form is a self-supporting film. In this embodiment, the film dosage includes a polymer carrier matrix, a therapeutically effective amount of buprenorphine, an agonist. The buffer is preferably capable of providing a local pH of the composition within a range that provides the desired level of absorption of the buprenorphine. The resulting dosage is a film composition that allows for a rapid and effective release of buprenorphine into the oral cavity of the user. At the same time, the film composition preferably has a sufficient adhesion profile, such that the film cannot easily be removed from the oral cavity of the user once it has been placed into the cavity. Full release of the buprenorphine preferably takes place within less than about thirty minutes, and preferably remains in the oral cavity for at least 1 minute.

As explained above, while providing a pharmaceutically acceptable level of an agonist is helpful in treating those with narcotic addiction, it may be desirable to provide the buprenorphine in combination with naloxone (an antagonist) so as to reduce the effect of the agonist and therefore aid in reducing dependency of the narcotic. Therefore, it may be desirable to combine the opioid agonist (or partial agonist) in the film composition with an opioid antagonist or a pharmaceutically acceptable salt thereof. The actives may be dispersed throughout the dosage separately or they may be combined together and dispersed into the dosage. Most desirably the antagonist includes naloxone, but any suitable basic antagonist may be selected as desired. The antagonist may optionally be water-soluble, so as to render separation of the antagonist and agonist difficult, thereby lessening the potential for abuse of the agonist.

As with a film including an agonist, the film including an agonist and an antagonist is desirably pH-controlled through the inclusion of a buffer. In such combination films, it has been discovered that the local pH of the film composition should preferably be in the range of about 2 to about 4, and more preferably about 3 to about 4 so as to provide a bioequivalent product as the commercially-available Suboxone® tablet. Most preferably the local pH of the film composition is about 3.5. At this local pH level, absorption of the buprenorphine is optimized while the absorption of the naloxone is inhibited.

The film may contain any desired level of self-supporting film forming polymer, such that a self-supporting film composition is provided. In one embodiment, the film composition contains a film forming polymer in an amount of at least 25% by weight of the composition. The film forming polymer may alternatively be present in an amount of at least 50% by weight of the composition. As explained above, any film forming polymers that impart the desired mucoadhesion and rate of film dissolution may be used as desired.

Any desired level of agonist and optional antagonist may be included in the dosage, so as to provide the desired effect. In one particular embodiment, the film composition includes about 2 mg to about 16 mg of agonist per dosage. More desirably, the film composition includes about 4 mg to about 12 mg of agonist per dosage. If desired, the film composition may include about 0.5 mg to about 5 mg of antagonist per dosage. More desirably, the film composition includes about 1 mg to about 3 mg of antagonist per dosage. If an antagonist is incorporated into the film, the film composition may include the antagonist in a ratio of about 6:1-2:1 agonist to antagonist. Most desirably, the film composition contains about 4:1 agonist to antagonist per dosage. For example, in one embodiment, the dosage includes an agonist in an amount of about 12 mg, and includes an antagonist in an amount of about 3 mg.

The film compositions further desirably contains a buffer so as to control the local pH of the film composition. Any desired level of buffer may be incorporated into the film composition so as to provide the desired local pH level. The buffer is preferably provided in an amount sufficient to control the release from the film and/or the absorption into the body of the agonist and the optional antagonist. In a desired embodiment, the film composition includes buffer in a ratio of buffer to agonist in an amount of from about 2:1 to about 1:5 (buffer:agonist). The buffer may alternatively be provided in a 1:1 ratio of buffer to agonist. As stated above, the film composition preferably has a local pH of about 2 to about 4, and most preferably has a local pH of about 3.5. Any buffer system may be used as desired. In some embodiments, the buffer may include sodium citrate, citric acid, and combinations thereof.

In this embodiment, the resulting film composition includes a polymer matrix, an agonist, and an optional antagonist, while the film composition has a controlled local pH to the level desired. The buffer is preferably present in an amount to provide a therapeutically adequate absorption of the agonist, while simultaneously limiting the absorption of the antagonist. Controlling of the local pH allows for the desired release and/or absorption of the components, and thus provides a more useful and effective dosage.

The film dosage composition may include a polymer carrier matrix, a therapeutically effective amount of agonist, a therapeutically effective amount of antagonist, and a buffering system. The buffering system may include a buffer in addition to a solvent. The buffering system desirably includes a sufficient level of buffer so as to provide a desired local pH level of the film dosage composition.

In addition to a desired local pH level, the buffer preferably has a buffer capacity sufficient to maintain the ionization of the optional antagonist during the time that the composition is in the oral cavity of a user. Maintaining the ionization of the antagonist serves to limit the absorption of the antagonist, and thus provide the desired control of the antagonist. While the ionization of the antagonist is limited, the ionization of the agonist may not be so limited. As such, the resulting dosage form provides absorption of the agonist to the user, while sufficiently reducing and/or preventing absorption of the antagonist. By keeping the antagonist ionized and the local pH at the optimum pH, the antagonist has limited if any absorption, but is still present should the product be abused or taken via a different route of administration. However, when taken as administered, the antagonist has little to no effect in blocking the agonist.

The film dosage composition including an agonist may be configured to provide an in vivo plasma profile having a mean maximum plasma concentration (Cmax) in a desired range. It has been discovered by the Applicants that controlling the Cmax of the film composition allows one to control the absorption of the active (such as an agonist) into the user. The resulting film composition is more effective and suitable for delivery to a user.

As explained, the film dosage composition provides a bioequivalent result to a commercially available Suboxone® product. As will be explained more in the Examples below, commercially available Suboxone® provides different absorption levels depending on the amount of buprenorphine and naloxone administered. The present invention desirably provides a film product providing bioequivalent release as that of the Suboxone® product. As with the Suboxone® product, the buprenorphine may be present in an amount of from about 2 mg to about 16 mg per dosage, or, if desired about 4 mg to about 12 mg per dosage. Additionally, the naloxone may be present in any desired amount, preferably at about 25% the level of buprenorphine. For example, an inventive film product may have 2 mg buprenorphine and 0.5 mg naloxone, 4 mg buprenorphine and 1 mg naloxone, 8 mg buprenorphine and 2 mg naloxone, 12 mg buprenorphine and 3 mg naloxone, 16 mg buprenorphine and 4 mg naloxone, or any similar amounts.

It has further been discovered that, by controlling the mean area under the curve (AUC) value of the film composition, a more effective dosage form may be provided. As is described in more detail in the Examples below, the inventive film composition preferably provides an AUC value so as to provide a bioequivalent result as that provided by the commercially available Suboxone® tablet. In one embodiment, the film composition may include a mean AUCinf value of about 6.8 hr·ng/ml or greater. Alternatively, the film composition may include a mean AUCinf value of from about 6.8 hr·ng/ml to about 66 hr·ng/ml.

As explained above, the film compositions may include naloxone, an antagonist. When the film composition includes a combination of agonist and antagonist, the film composition may be configured to provide a particular Cmax and/or AUCinf for the antagonist. For example, when a buprenorphine agonist and a naloxone antagonist are incorporated into the film composition, the naloxone may be configured to provide a Cmax of less than about 400 pg/ml, less than about 318 pg/ml, less than about 235 pg/ml, less than about 92 pg/ml or less than about 64 pg/ml. In such films, the naloxone may provide a mean AUCinf value of less than about 1030 hr·ng/ml.

In formulations which include an agonist in combination with an antagonist, the film composition may be prepared to provide a desired Cmax and/or AUCinf value for each of the agonist and antagonist. In one embodiment, the film composition provides an in vivo plasma profile having a Cmax of less than about 6.4 ng/ml for the agonist and an in vivo plasma profile having a Cmax of less than about 400 pg/ml for the antagonist. In such embodiments, the formulation may provide an AUCinf value of more than about 6.8 hr·ng/ml for the agonist. If desired, the formulation may provide an AUCinf value of less than about 1030 hr·pg/ml for the antagonist. Such compositions may include the agonist and the antagonist in any desired amount, and in a preferred embodiment, the composition includes about 2 mg to about 16 mg of the agonist per dosage and about 0.5 mg to about 4 mg of the antagonist per dosage.

The present invention provides a method of treating narcotic dependence in a patient. In one embodiment, the patient is dependent on opioid narcotics, but the patient may have a dependence on non-opioid narcotics. Desirably, the patient is treated by providing a dosage to the patient, which provides an effective release of actives but simultaneously provides a suitable adhesion so that the dosage cannot be easily removed. In one method of treatment, an orally dissolvable film composition is provided to a patient.

Depending on the particular narcotic that the patient experiences dependence upon, the film composition may include one or more particular active components. In one embodiment, the film composition includes a polymer carrier matrix and a therapeutically effective amount of an agonist. Desirably the agonist is a partial agonist. For opioid dependency, the agonist may be an opioid agonist, such as buprenorphine or a pharmaceutically acceptable salt thereof. The film composition preferably includes a buffer in an amount sufficient to control the local pH of the film composition. Any buffer system may be used, including sodium citrate, citric acid, and combinations thereof. In compositions solely including an agonist, the local pH of the film composition is desirably about 5 to about 6.5, and most desirably the local pH is about 5.5. At this level, the absorption of the agonist is most effective. To treat the dependency, the film composition is administered to the patient, most desirably into the oral cavity of the patient.

If desired, the composition may include a therapeutically effective amount of an antagonist, to prevent abuse of the agonist. A "therapeutically effective amount" of an antagonist is intended to refer to an amount of the antagonist that may be useful in diverting abuse of the agonist by a user. The antagonist may be any desired antagonist, and in one embodiment includes naloxone or a pharmaceutically acceptable salt thereof. The film composition is preferably administered to a patient through the oral cavity of the patient, but may be administered in any desired means. The orally dissolvable film composition is then allowed to dissolve in the oral cavity of the patient for a sufficient time so as to release the active(s) therein. In some embodiments, the film composition may remain in the oral cavity for at least 30 seconds, and in some embodiments may remain in the oral cavity for at least 1 minute. After the film composition is placed into the oral cavity of the patient, the film preferably becomes sufficiently adhered so as to render its removal difficult. After the film composition has been administered to the patient, the active(s) are sufficiently released from the composition and allowed to take effect on the patient.

The film compositions of the present invention may be formed via any desired process. Suitable processes are set forth in U.S. Pat. Nos. 7,425,292 and 7,357,891, the entire contents of which are incorporated by reference herein. In one embodiment, the film dosage composition is formed by first preparing a wet composition, the wet composition including a polymeric carrier matrix, a therapeutically effective amount of an agonist, and a buffer in an amount sufficient to control the local pH of the composition to a desired level. The wet composition is cast into a film and then sufficiently dried to form a self-supporting film composition. The wet composition may be cast into individual dosages, or it may be cast into a sheet, where the sheet is then cut into individual dosages. The agonist may be a partial agonist. If desired, the wet composition may include a therapeutically effective amount of an antagonist.

The agonist and the optional antagonist are preferably selected to treat a particular narcotic dependency. For opioid dependency, for example, the agonist may include buprenorphine or a pharmaceutically acceptable salt thereof, while the antagonist may include naloxone or a pharmaceutically acceptable salt thereof. The local pH of the film composition is desirably maintained at about 2 to about 4.

EXAMPLES

Example 1—Composition of Buprenorphine/Naloxone Films at Various Strengths

Film strips including a combination of buprenorphine and naloxone were prepared. Four different strength film compositions were prepared, which include a ratio of buprenorphine to naloxone of 16/4, 12/3, 8/2, and 2/0.5. The compositions are summarized in Table 1 below.

TABLE 1

Various Compositions of Film Dosages

| Components | Buprenorphine/Naloxone Films Unit Formula (mg per film strip) | | | |
| --- | --- | --- | --- | --- |
| Buprenorphine/Naloxone Ratios | 16/4 | 12/3 | 8/2 | 2/0.5 |
| Active Components | | | | |
| Buprenorphine HCl | 17.28 | 12.96 | 8.64 | 2.16 |
| Naloxone HCl Dihydrate | 4.88 | 3.66 | 2.44 | 0.61 |
| Inactive Components | | | | |
| Polyethylene Oxide, NF (MW 200,000) | 27.09 | 20.32 | 13.55 | — |
| Polyethylene Oxide, NF (MW 100,000) | 12.04 | 9.03 | 6.02 | 19.06 |
| Polyethylene Oxide, NF (MW 900,000) | 4.82 | 3.62 | 2.41 | 2.05 |
| Malitol, NF | 12.04 | 9.03 | 6.02 | 5.87 |
| Flavor | 6.0 | 4.5 | 3.0 | 2.4 |
| Citric Acid, USP | 5.92 | 4.44 | 2.96 | 2.96 |
| HPMC | 4.22 | 3.16 | 2.11 | 2.34 |
| Ace-K | 3.0 | 2.25 | 1.5 | 1.2 |
| Sodium Citrate, anhydrous | 2.68 | 2.01 | 1.34 | 1.34 |
| Colorant | 0.03 | 0.02 | 0.01 | 0.01 |
| Total (mg) | 100 | 75 | 50 | 40 |

Example 2—Absorption Studies for Suboxone® Products

Various film and tablet products were prepared and tested for absorption data, including Cmax and AUC absorption levels. The products tested included Suboxone® tablets made with either 2 mg or 16 mg buprenorphine as well as either 0.5 mg or 4.0 mg naloxone. For 16 mg buprenorphine tablets, two 8 mg buprenorphine tablets were combined together to provide the level of components of a 16 mg buprenorphine tablet. In instances where a 12 mg buprenorphine tablet was evaluated, this dosage was obtained by combining one 8 mg buprenorphine tablet and two 2 mg buprenorphine tablets. These products were tested for absorption levels, with the amounts listed in Table 2 below.

TABLE 2

Absorption Data for Suboxone ® products

| Sample | C max | AUC |
|---|---|---|
| Buprenorphine (2 mg) Suboxone ® Tablet | 0.780 ng/ml | 6.789 hr*ng/ml |
| Naloxone (0.5 mg) Suboxone ® Tablet | 51.30 pg/ml | 128.60 hr*pg/ml |
| Buprenorphine (16 mg) Suboxone ® Tablet | 4.51 ng/ml | 44.99 hr*ng/ml |
| Naloxone (4 mg) Suboxone ® Tablet | 259.00 pg/ml | 649.60 hr*pg/ml |

Using the data from Table 2, absorption data for the Suboxone® tablets for other levels of buprenorphine and naloxone are set forth in Table 2A below.

TABLE 2A

Extrapolated Absorption Data for Suboxone ® products

| Sample | C max | AUC |
|---|---|---|
| Buprenorphine (4 mg) Suboxone ® Tablet | 1.35 ng/ml | 12.25 hr*ng/ml |
| Naloxone (1 mg) Suboxone ® Tablet | 80.97 pg/ml | 203 hr*pg/ml |
| Buprenorphine (8 mg) Suboxone ® Tablet | 2.29 ng/ml | 23.17 hr*ng/ml |
| Naloxone (2 mg) Suboxone ® Tablet | 140.31 pg/ml | 351.8 hr*pg/ml |
| Buprenorphine (12 mg) Suboxone ® Tablet | 3.23 ng/ml | 34.08 hr*ng/ml |
| Naloxone (3 mg) Suboxone ® Tablet | 199.7 pg/ml | 500.6 hr*pg/ml |

Example 3—Evaluation of Bioequivalence of Suboxone® Tablets

Using the data generated for Suboxone® tablets in Table 2 above, acceptable bioequivalence ranges are generated to provide an equivalent treatment level as the Suboxone® tablet. As currently understood, a product provides a bioequivalent effect if it provides absorption levels between about 80% to about 125% of the Suboxone® tablet. Absorption in this range is considered to be bioequivalent.

TABLE 3

Acceptable Bioequivalence Ranges for Suboxone ® Tablets (80 to 125%)

| Description of Sample | C max | AUC |
|---|---|---|
| Buprenorphine 2 mg | 0.624 to 0.975 ng/ml | 5.431 to 8.486 hr*ng/ml |
| Naloxone 0.5 mg | 41.04 to 64.13 pg/ml | 102.88 to 160.75 hr*pg/ml |
| Buprenorphine 16 mg | 3.608 to 5.638 ng/ml | 35.992 to 56.238 hr*ng/ml |
| Naloxone 4 mg | 207.20 to 323.75 pg/ml | 519.68 to 812.00 hr*pg/ml |

Thus, to be considered bioequivalent to the Suboxone® tablet, the Cmax of buprenorphine is between about 0.624 and 5.638, and the AUC of buprenorphine is between about 5.431 to about 56.238. Similarly, to be considered bioequivalent to the Suboxone® tablet, the Cmax of naloxone is between about 41.04 to about 323.75, and the AUC of naloxone is between about 102.88 to about 812.00.

Example 4—Absorption Studies for Film Products at pH 3.5

Various film products were prepared and tested for absorption data, including Cmax and AUC absorption levels. The products tested included inventive film strips, the film strips having either 2 mg or 16 mg buprenorphine as well as either 0.5 mg or 4.0 mg naloxone. These products were tested for absorption levels, with the amounts listed in Table 4 below.

TABLE 4

Adsorption Data for inventive film products at pH 3.5

| Sample | C max | AUC |
|---|---|---|
| Buprenorphine (2 mg) Sublingual Film | 0.947 ng/ml | 7.82 hr*ng/ml |
| Naloxone (0.5 mg) Sublingual Film | 51.10 pg/ml | 128.60 hr*pg/ml |
| Buprenorphine (16 mg) Sublingual Film | 5.47 ng/ml | 55.30 hr*ng/ml |
| Naloxone (4 mg) Sublingual Film | 324.00 pg/ml | 873.60 hr*pg/ml |

As can be seen, in this experiment, the values for buprenorphine absorbance were squarely in the bioequivalence range evaluated above. The inventive films were therefore determined to have provided a bioequivalent absorption of buprenorphine at a local pH of 3.5 as the commercially available Suboxone® tablet. The values for absorption of naloxone were very close to the bioequivalent range of Suboxone®. The slightly higher absorption of Naloxone was not due to the local pH but rather to the amount of buffer (buffer capacity as discussed in the application). This is confirmed by the fact that the lower 2/0.5 mg dose is in range for the Naloxone and this is due to the higher buffer capacity for the 2/0.5 dose as pointed out in the buffer capacity chart.

Example 5—Preparation of Films for In Vivo Study

Film dosages were prepared for use in an in vivo study to determine the bioavailability of buprenorphine/naloxone tablets and film formulations. Specifically, the films were tested to determine whether the film provides a bioequivalent effect to that of a tablet formulation.

Three film formulations including 8 mg buprenorphine and 2 mg naloxone were prepared, each being buffered to a different pH. The first film did not include any buffer, providing a local pH of about 6.5. The second was buffered to a local pH level of about 3-3.5. The third was buffered to a local pH value of about 5-5.5. The formulations are set forth in Table 5 below.

TABLE 5

Formulations of Test Films at Various pH Levels

| Component | Test formulation 1 8 mg/2 mg pH = 6.5 | | Test formulation 2 8 mg/2 mg pH = 3-3.5 | | Test formulation 3 8 mg/2 mg pH = 5-5.5 | |
|---|---|---|---|---|---|---|
| | % w/w | Mg/film | % w/w | Mg/film | % w/w | Mg/film |
| Buprenorphine HCl | 21.61 | 8.64 | 17.28 | 8.64 | 17.28 | 8.64 |

TABLE 5-continued

Formulations of Test Films at Various pH Levels

| Component | Test formulation 1 8 mg/2 mg pH = 6.5 | | Test formulation 2 8 mg/2 mg pH = 3-3.5 | | Test formulation 3 8 mg/2 mg pH = 5-5.5 | |
|---|---|---|---|---|---|---|
| | % w/w | Mg/film | % w/w | Mg/film | % w/w | Mg/film |
| Naloxone HCl Dihydrate | 6.10 | 2.44 | 4.88 | 2.44 | 4.88 | 2.44 |
| Polymer | 5.05 | 2.02 | 4.82 | 2.41 | 4.82 | 2.41 |
| Polymer | 28.48 | 11.39 | 27.09 | 13.55 | 27.09 | 13.55 |
| Polymer | 12.65 | 5.06 | 12.04 | 6.02 | 12.04 | 6.02 |
| Polymer | 4.43 | 1.77 | 4.22 | 2.11 | 4.22 | 2.11 |
| Sweetener | 12.65 | 5.06 | 12.04 | 6.02 | 12.04 | 6.02 |
| Sweetener | 3 | 1.2 | 3 | 1.5 | 3 | 1.5 |
| Flavor | 6 | 2.4 | 6 | 3 | 6 | 3 |
| Citric acid | 0 | 0 | 5.92 | 2.96 | 2.51 | 1.26 |
| Sodium citrate | 0 | 0 | 2.68 | 1.34 | 6.08 | 3.04 |
| FD&C yellow #6 | 0.025 | 0.01 | 0.03 | 0.02 | 0.03 | 0.02 |
| Total | 100 | 40 | 100 | 50 | 100 | 50 |

Example 6—Analysis of In Vivo Absorption of Film Having a pH of 6.5

The film dosage composition of film having a local pH of 6.5 was analyzed. Specifically, Test Formulation 1, as prepared in Example 5 was analyzed in vivo to determine the absorption of buprenorphine and of naloxone. The comparative film was compared to the absorption of buprenorphine and of naloxone provided by a one dose tablet (Suboxone®). The test film was compared to determine whether it provided a bioequivalent effect as the tablet product.

The results for Test Formulation 1, which had a local pH of about 6.5, as compared to the one dose tablet, are set forth in Tables 6 and 7 below.

TABLE 6

Buprenorphine In Vivo Absorption Data for Test Formulation 1

| Parameter | Suboxone ® sublingual | | | | Test Formulation 1 (pH = 6.5) | | | |
|---|---|---|---|---|---|---|---|---|
| | n | Mean | SD | CV % | n | Mean | SD | CV % |
| $T_{max}$ (hr) | 15 | 1.60 | 0.47 | 29.41 | 15 | 1.50 | 0.62 | 41.23 |
| $C_{max}$ (ng/mL) | 15 | 2.27 | 0.562 | 24.77 | 15 | 2.60 | 0.872 | 33.53 |
| $AUC_{last}$ (hr*ng/mL) | 15 | 27.08 | 10.40 | 38.41 | 15 | 31.00 | 12.93 | 41.72 |
| $AUC_{inf}$ (hr*ng/mL) | 15 | 29.58 | 11.15 | 37.68 | 15 | 33.37 | 13.88 | 41.61 |
| $T_{1/2}$ (hr) | 15 | 44.76 | 20.86 | 46.60 | 15 | 40.73 | 14.93 | 36.66 |

TABLE 7

Naloxone In Vivo Absorption Data for Test Formulation 1

| Parameter | Suboxone ® sublingual | | | | Test Formulation 1 (pH = 6.5) | | | |
|---|---|---|---|---|---|---|---|---|
| | n | Mean | SD | CV % | n | Mean | SD | CV % |
| $T_{max}$ (hr) | 15 | 0.90 | 0.23 | 25.32 | 15 | 0.68 | 0.18 | 25.75 |
| $C_{max}$ (pg/mL) | 15 | 94.6 | 39.1 | 41.33 | 15 | 410 | 122 | 29.75 |
| $AUC_{last}$ (hr*pg/mL) | 15 | 297.1 | 120.7 | 40.62 | 15 | 914.8 | 158.1 | 17.29 |
| $AUC_{inf}$ (hr*pg/mL) | 15 | 306.1 | 122.6 | 40.06 | 15 | 924.2 | 158.8 | 17.18 |
| $T_{1/2}$ (hr) | 15 | 6.62 | 2.60 | 39.26 | 15 | 6.86 | 2.08 | 30.27 |

As can be seen, the in vivo data indicates that buprenorphine is absorbed very well from the film formulation at a local pH of 6.5, and matched closely the absorption seen in the Suboxone® one dose tablet. However, the absorption was also maximized for the naloxone, which was undesirable. It was determined that a film having a combination of buprenorphine and naloxone and a local pH of 6.5 did not provide a bioequivalent effect as the Suboxone® tablet for both buprenorphine and naloxone.

Example 7—Analysis of In Vivo Absorption of Film Having a pH of 5-5.5

Having determined the absorption of buprenorphine and naloxone in film having a local pH of 6.5, a film dosage composition of film having a local pH of 5-5.5 was analyzed. Specifically, Test Formulation 3, as prepared in Example 5 was analyzed in vivo to determine the absorption of buprenorphine and of naloxone. The comparative films were compared to the absorption of buprenorphine and of naloxone provided by the Suboxone® one dose tablet. The test film was compared to determine whether it provided a bioequivalent effect as the Suboxone® tablet.

The results for Test Formulation 3, which had a local pH of about 5-5.5, as compared to the Suboxone® tablet, are set forth in Tables 8 and 9 below.

TABLE 8

Buprenorphine In Vivo Absorption Data for Test Formulation 3

| Parameter | Suboxone ® sublingual | | | | Test Formulation 3 (pH = 5-5.5) | | | |
|---|---|---|---|---|---|---|---|---|
| | n | Mean | SD | CV % | n | Mean | SD | CV % |
| $T_{max}$ (hr) | 15 | 1.60 | 0.47 | 29.41 | 14 | 1.50 | 0.43 | 28.50 |
| $C_{max}$ (ng/mL) | 15 | 2.27 | 0.562 | 24.77 | 14 | 3.47 | 1.57 | 45.40 |
| $AUC_{last}$ (hr*ng/mL) | 15 | 27.08 | 10.40 | 38.41 | 14 | 33.25 | 16.01 | 48.16 |
| $AUC_{inf}$ (hr*ng/mL) | 15 | 29.58 | 11.15 | 37.68 | 13 | 38.34 | 15.38 | 40.13 |
| $T_{1/2}$ (hr) | 15 | 44.76 | 20.86 | 46.60 | 13 | 41.71 | 17.70 | 42.42 |

TABLE 9

Naloxone In Vivo Absorption Data for Test Formulation 3

| Parameter | Suboxone® sublingual | | | | Test Formulation 3 (pH = 5-5.5) | | | |
|---|---|---|---|---|---|---|---|---|
| | n | Mean | SD | CV % | n | Mean | SD | CV % |
| $T_{max}$ (hr) | 15 | 0.90 | 0.23 | 25.32 | 14 | 0.98 | 0.62 | 63.51 |
| $C_{max}$ (pg/mL) | 15 | 94.6 | 39.1 | 41.33 | 14 | 173 | 84.5 | 48.79 |
| $AUC_{last}$ (hr*pg/mL) | 15 | 297.1 | 120.7 | 40.62 | 14 | 455.2 | 195.5 | 42.94 |
| $AUC_{inf}$ (hr*pg/mL) | 15 | 306.1 | 122.6 | 40.06 | 13 | 474.4 | 203.1 | 42.81 |
| $T_{1/2}$ (hr) | 15 | 6.62 | 2.60 | 39.26 | 13 | 9.45 | 6.90 | 73.00 |

As can be seen, the in vivo data indicated that the absorption of buprenorphine increased as the local pH level decreased. It appeared that by decreasing the local pH from 6.5 to 5.5, the absorption of buprenorphine was being moved to a level further away from that of the one dose tablet. In addition, the naloxone values did not provide a bioequivalent result as the one dose tablet. Thus, it was determined that the film having a local pH of 5.5 did not provide a bioequivalent result as that of the Suboxone® tablet for both buprenorphine and naloxone.

It was noted that by reducing the local pH of the film to a level of 5.5, there would be provided an increased level of absorption of buprenorphine. Thus, it may be desirable to buffer a film composition incorporating buprenorphine itself to a level of about 5.5 to provide an increased absorption.

Example 8—Analysis of In Vivo Absorption of Film Having a pH of 3-3.5

Having determined the absorption of buprenorphine and naloxone in films having a local pH of 6.5 and 5.5, a film dosage composition of film having a local pH of about 3-3.5 was analyzed. It was assumed that the absorption of buprenorphine would continue to be increased as it had demonstrated at a local pH of 5.5. Thus, it was assumed that at a local pH of 3.5, the film would not be bioequivalent to that of the tablet.

Specifically, Test Formulation 2, as prepared in Example 5, was analyzed in vivo to determine the absorption of buprenorphine and of naloxone. The comparative films were compared to the absorption of buprenorphine and of naloxone provided by the Suboxone® one dose tablet. The test film was compared to determine whether it provided a bioequivalent effect as the tablet product.

The results for Test Formulation 2, which had a local pH of about 3-3.5, as compared to the Suboxone® tablet, are set forth in Tables 10 and 11 below.

TABLE 10

Buprenorphine In Vivo Absorption Data for Test Formulation 2

| Parameter | Suboxone® sublingual | | | | Test Formulation 2 (pH = 3-3.5) | | | |
|---|---|---|---|---|---|---|---|---|
| | n | Mean | SD | CV % | n | Mean | SD | CV % |
| $T_{max}$ (hr) | 15 | 1.60 | 0.47 | 29.41 | 14 | 1.68 | 0.58 | 34.68 |
| $C_{max}$ (ng/mL) | 15 | 2.27 | 0.562 | 24.77 | 14 | 2.68 | 0.910 | 33.99 |
| $AUC_{last}$ (hr*ng/mL) | 15 | 27.08 | 10.40 | 38.41 | 14 | 29.73 | 12.05 | 40.54 |
| $AUC_{inf}$ (hr*ng/mL) | 15 | 29.58 | 11.15 | 37.68 | 14 | 31.45 | 12.98 | 41.26 |
| $T_{1/2}$ (hr) | 15 | 44.76 | 20.86 | 46.60 | 14 | 30.03 | 13.95 | 46.46 |

TABLE 11

Naloxone In Vivo Absorption Data for Test Formulation 2

| Parameter | Suboxone® sublingual | | | | Test Formulation 2 (pH = 3-3.5) | | | |
|---|---|---|---|---|---|---|---|---|
| | n | Mean | SD | CV % | n | Mean | SD | CV % |
| $T_{max}$ (hr) | 15 | 0.90 | 0.23 | 25.32 | 14 | 0.84 | 0.19 | 22.19 |
| $C_{max}$ (pg/mL) | 15 | 94.6 | 39.1 | 41.33 | 14 | 130 | 72.9 | 56.04 |
| $AUC_{last}$ (hr*pg/mL) | 15 | 297.1 | 120.7 | 40.62 | 14 | 362.2 | 155.9 | 43.03 |
| $AUC_{inf}$ (hr*pg/mL) | 15 | 306.1 | 122.6 | 40.06 | 12 | 350.4 | 142.3 | 40.61 |
| $T_{1/2}$ (hr) | 15 | 6.62 | 2.60 | 39.26 | 12 | 8.07 | 4.75 | 58.84 |

As can be seen, the in vivo data indicated that the absorption of buprenorphine was substantially bioequivalent to that of the one dose tablet when the film composition local pH was lowered to about 3-3.5. This result was surprising as it did not appear to follow the pH partition theory. Further, at a local pH of about 3-3.5, it was seen that the absorption of naloxone was substantially bioequivalent to that of the one dose tablet.

Thus, it was determined that the film product including buprenorphine and naloxone at a local pH of 3-3.5 was substantially bioequivalent to that of the Suboxone® one dose tablet.

Example 9—Normalized Values for Naloxone in Films and Tablets

Various film compositions including buprenorphine and naloxone in 8/2 mg and 2/0.5 mg dosages, and having different local pH values from 6.5 to 3.5, were prepared and analyzed. The data was normalized and compared to the one dose tablet. The results are set forth in Table 12 below.

TABLE 12

Normalized Values for Naloxone Film Compared to Tablet

| pH | Dose (mg) Buprenorphine/ Naloxone | AUC (Normalized) | Cmax | Mg Citric Acid | Ratio Citric Acid (mg)/ Naloxone (mg) |
|---|---|---|---|---|---|
| 6.5 | 8/2 | 3.02 | 4.33 | 1.34 | 0.67 |
| 5.5 | 8/2 | 1.55 | 1.83 | 1.34 | 0.67 |
| 3.5 | 8/2 | 1.14 | 1.37 | 1.34 | 0.67 |

TABLE 12-continued

Normalized Values for Naloxone Film Compared to Tablet

| pH | Dose (mg) Buprenorphine/ Naloxone | AUC (Normalized) | Cmax | Mg Citric Acid | Ratio Citric Acid (mg)/ Naloxone (mg) |
|---|---|---|---|---|---|
| 3.5 | 2/0.5 | 0.98 | 0.90 | 1.34 | 2.68 |
| 5.5 | 2/0.5 | 1.41 | 1.41 | 1.34 | 2.68 |

The data indicates that not only is the local pH of significant importance, but the amount of buffer present in the formula is also important. The improvement from the 8/2 dose to the 2/0.5 dose (at a local pH of 3.5) demonstrates this importance. The 8/2 dose has a ratio of buffer/naloxone of 0.67, and this dose provided borderline acceptable bioequivalent results. In contrast, the 2/0.5 dose has a ratio of buffer/naloxone of 2.68, and provides a more bioequivalent absorption value than the 8/2 dose.

In fact, the data shows that the 2/0.5 dose at a local pH of 3.5 had an even lower buccal absorption than the one dose tablet, as seen from the normalized values for the AUC and Cmax. This demonstrates that even less absorption of the naloxone occurs for the film formulation at a local pH of 3.5 than the tablet formulation. Given the goal of reducing the absorption of naloxone, it appears that the film product buffered at a local pH of 3.5 with a buffer ratio of buffer/Naloxone of 2.68 provides even better results than the Suboxone® tablet formulation.

What is claimed is:

1. An oral, self-supporting, mucoadhesive film comprising:
   (a) at least 25 wt % of a water-soluble polymeric matrix;
   (b) about 2 mg to about 16 mg of buprenorphine or a pharmaceutically acceptable salt thereof;
   (c) about 0.5 mg to about 4 mg of naloxone or a pharmaceutically acceptable salt thereof; and
   (d) an acidic buffer;
   wherein the film is mucoadhesive to the sublingual mucosa or the buccal mucosa;
   wherein the weight ratio of (b):(c) is about 4:1;
   wherein the weight ratio of (d):(b) is from 2:1 to 1:5; and
   wherein application of the film on the sublingual mucosa or the buccal mucosa results in differing absorption between buprenorphine and naloxone, with a buprenorphine $C_{max}$ from about 0.624 ng/ml to about 5.638 ng/ml and a buprenorphine AUC from about 5.431 hr*ng/ml to about 56.238 hr*ng/ml; and a naloxone $C_{max}$ from about 41.04 pg/ml to about 323.75 pg/ml and a naloxone AUC from about 102.88 hr*pg/ml to about 812.00 hr*pg/ml.

2. The film of claim 1, wherein the weight ratio of (d):(b) is from about 1:1 to 1:5.

3. The film of claim 1, wherein the weight ratio of (d):(b) is from about 1.4:1 to about 1:3.

4. The film of claim 1, wherein the acidic buffer is citric acid.

5. The film of claim 1, comprising at least 50 wt % of the water-soluble polymeric matrix.

6. The film of claim 1, wherein the water-soluble polymeric matrix comprises a polyethylene oxide polymer alone or in combination with a hydrophilic cellulosic polymer.

7. The film of claim 6, wherein the hydrophilic cellulosic polymer is hydroxypropyl cellulose, hydroxypropylmethyl cellulose, or a combination thereof.

8. The film of claim 7, wherein the hydrophilic cellulosic polymer is hydroxypropylmethyl cellulose.

9. A method for treating opioid dependence in a patient in need thereof comprising sublingually or buccally administering the mucoadhesive film of claim 1 to a sublingual or buccal mucosal tissue of the patient to treat the opioid dependence.

* * * * *